(12) United States Patent
Dalko et al.

(10) Patent No.: US 11,420,960 B2
(45) Date of Patent: Aug. 23, 2022

(54) USE OF 5-OXAZOLIDINE-2,4-DIONE C-GLYCOSIDE DERIVATIVES AS MOISTURIZER FOR THE SKIN

(71) Applicant: L'OREAL, Paris (FR)

(72) Inventors: Maria Dalko, Aulnay-sous-Bois (FR); Amélie Prevot-Gueguiniat, Aulnay-sous-Bois (FR); Marie-céline Frantz, Aulnay-sous-Bois (FR); Sébastien Dropsit, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/973,887

(22) PCT Filed: Jun. 19, 2019

(86) PCT No.: PCT/EP2019/066161
§ 371 (c)(1),
(2) Date: Dec. 10, 2020

(87) PCT Pub. No.: WO2020/002076
PCT Pub. Date: Jan. 2, 2020

(65) Prior Publication Data
US 2021/0276989 A1    Sep. 9, 2021

(30) Foreign Application Priority Data

Jun. 29, 2018 (FR) ...................... 1856029

(51) Int. Cl.
| | | |
|---|---|---|
| *C07D 413/04* | (2006.01) |
| *A61K 8/60* | (2006.01) |
| *A61Q 19/00* | (2006.01) |
| *C07D 405/04* | (2006.01) |
| *C07H 1/00* | (2006.01) |
| *C07H 7/06* | (2006.01) |

(52) U.S. Cl.
CPC ............ *C07D 413/04* (2013.01); *A61K 8/602* (2013.01); *A61Q 19/007* (2013.01); *C07D 405/04* (2013.01); *C07H 1/00* (2013.01); *C07H 7/06* (2013.01)

(58) Field of Classification Search
None
See application file for complete search history.

(56) References Cited

U.S. PATENT DOCUMENTS

| | | |
|---|---|---|
| 2004/0048785 A1 | 3/2004 | Dalko et al. |
| 2010/0168049 A1 | 7/2010 | Laboureau et al. |
| 2013/0261077 A1 | 10/2013 | Bennani et al. |
| 2019/0263770 A1 | 8/2019 | Frantz et al. |
| 2019/0274940 A1 | 9/2019 | Frantz et al. |

FOREIGN PATENT DOCUMENTS

| | | |
|---|---|---|
| FR | 3 058 417 A1 | 5/2018 |
| JP | 2004-525877 A | 8/2004 |
| JP | 2010-155834 A | 7/2010 |
| WO | WO 2012/079938 A1 | 6/2012 |
| WO | WO 2018/083341 A1 | 5/2018 |
| WO | WO 2018/088341 A1 | 5/2018 |

OTHER PUBLICATIONS

Frantz, Org. Lett. 2019, 21, 2684-2687, published Mar. 27, 2019. (Year: 2019).*
Supporting information for Frantz, Org. Lett. 2019, 21, 2684-2687, published Mar. 27, 2019. (Year: 2019).*
Gama et al., "Silver Ion Mediated Desulfurization-Condensation of Glucosyl Isothiocyanate with Hydroxy Acids", Journal of Carbohydrate Chemistry, vol. 19, No. 2, Jan. 2000, pp. 119-126.
Roush et al., Stereoselective N-Acylation Reactions of [a]-Alkoxy Carbamates:, Journal of Organic Chemistry, vol. 63, No. 7, Apr. 1998 pp. 2062-2063.

* cited by examiner

*Primary Examiner* — Layla D Berry
(74) *Attorney, Agent, or Firm* — Polsinelli PC

(57) ABSTRACT

The present invention relates to the cosmetic use, as moisturizer for keratin materials, preferably the skin, of one or more 5-oxazolidine-2,4-dione C-glycoside derivatives corresponding to formula (I) below, and also the solvates and/or the isomers (optical, geometric, tautomers) thereof and/or the salts thereof: (I)

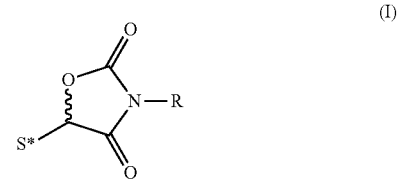

20 Claims, No Drawings

USE OF 5-OXAZOLIDINE-2,4-DIONE C-GLYCOSIDE DERIVATIVES AS MOISTURIZER FOR THE SKIN

CROSS REFERENCE TO RELATED APPLICATIONS

This application is a National Phase filing under 35 U.S.C. § 371 of PCT/EP2019/066161 filed on 19 Jun. 2019; which application in turn claims priority to Application No. 1856029 filed in France on 29 Jun. 2018. The entire contents of each application are hereby incorporated by reference.

The present invention relates to novel C-glycoside compounds, to a cosmetic composition comprising same, to a preparation process, to the use of said C-glycosides for treating keratin materials and in particular the skin, and to a process for treating keratin materials using said C-glycosides.

More particularly, the invention relates to the use of 5-oxazolidine-2,4-dione C-glycoside derivatives in the field of caring for keratin materials such as the skin, and especially as a moisturizer for keratin materials, preferably the skin.

The skin, which is a protective and exchange barrier with the environment, is both strong and fragile, it may lose its suppleness and its capacity to retain water decreases, then causing skin dryness.

It is known that the stratum corneum or corneal layer, which is the outermost region of the epidermis, is most particularly involved in moisturizing the skin. Located at the interface with the external environment, its function is especially to delay excessive water loss arising from the deeper layers of the epidermis. The stratum corneum also protects against mechanical attack. It also constitutes the first line of defense against UV radiation.

With a thickness of 10 µm, it is composed of vertically stacked corneocytes surrounded by a matrix of lipid-enriched membranes. Thus, it is a two-compartment system that may be compared to a wall of bricks, composed of anuclear cells (the "bricks") and of intercellular lamellar membranes (the "cement"). By virtue of this compact stratified structure, the stratum corneum performs its barrier function by opposing transcutaneous water loss. It thus efficiently contributes towards the moisturization of the skin via its capacity to take up and retain water, which is mainly located in the intercellular spaces.

For obvious reasons, it is important to ensure a sufficient level of skin moisturization in order to preserve its suppleness, softness, tonicity and/or appearance. In general, a decrease in this level of moisturization may be prevented or treated by acting on the stratum corneum via moisturizers, for instance glycerol, which are the reference active agents in this field.

However, drawbacks are observed with active agents of these types.

For example, glycerol has the drawback of making formulations tacky, especially when it is used in high concentration. There is thus a need to find other active agents in the field of skin moisturization that are free of the abovementioned drawbacks.

The inventors have discovered that 5-oxazolidine-2,4-dione C-glycoside derivatives of general formula (I) as described below are good moisturizers, and especially have a beneficial effect in terms of elasticity of the stratum corneum and/or improve the barrier function.
The 5-oxazolidine-2,4-dione C-glycoside derivatives of general formula (I), which are the subject of the present invention, make it possible especially to provide, while at the same time having a moisturizing effect, compositions that have good stability and/or that remain pleasant for the consumer, i.e. being sparingly tacky, having a pleasant feel, and/or having no discomfort sensations such as tautness.

Thus, the subject of the present invention is the cosmetic use of one or more 5-oxazolidine-2,4-dione C-glycoside derivatives corresponding to the formula (I) below, and also the solvates thereof such as hydrates, the optical and geometric isomers and tautomers thereof and the organic or mineral base or acid salts thereof,

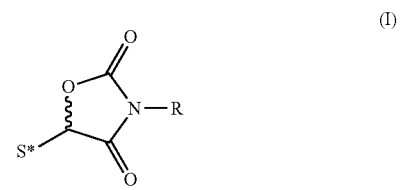

in which formula (I):
S* denotes a monosaccharide sugar radical or denotes a polysaccharide sugar radical comprising from 2 to 5 saccharide units, each saccharide unit (the saccharide unit in the case of a monosaccharide or each saccharide unit in the case of polysaccharides) comprising one or more hydroxyl groups optionally substituted with a radical R' chosen from:
i) $(C_1-C_6)$alkyl or $(C_2-C_6)$alkenyl; or
ii) an acetyl radical; or
iii) a protective group (PG) for hydroxyl function(s), such as $(C_2-C_6)$alkyl(thio)carbonyl or benzyl;
said monosaccharide radical possibly also being deoxygenated in position 2 (on its $C_2$ carbon atom);
said monosaccharide or polysaccharide radical possibly also comprising one or more amino groups $NR_bR_c$ with $R_b$ and $R_c$, which may be identical or different, representing a hydrogen atom, or an acetyl group, or a protective group for the amino function, such as $(C_2-C_6)$alkyl(thio)carbonyl;
said monosaccharide or polysaccharide radical being connected to the rest of the molecule by a bond between the $C_1$ carbon atom of one of the sugars of said monosaccharide or polysaccharide radical, this bond possibly being α or β anomeric;
R represents
i) a hydrogen atom;
ii) a $(C_1-C_{18})$alkyl group;
iii) an aryl$(C_1-C_4)$alkyl group optionally substituted with at least one hydroxyl and/or $(C_1-C_4)$alkoxy group, such as benzyl;
iv) a cycloalkyl group,
as a moisturizer for keratin materials, preferably the skin, and especially for treating dry skin.

The compounds of formula (I) make it possible to maintain and/or stimulate the moisturization and/or combat the drying out of keratin materials, such as the skin.

The compound(s) of formula (I) according to the invention, or the compositions comprising them, may be used once or repeatedly, such as one to two times per day, preferably once a day, preferably over a period of at least one week, and more particularly of at least four weeks.

The compound(s) of formula (I) thus defined may be used, alone or as mixtures, as moisturizer, in a composition comprising a physiologically acceptable medium, in particular a cosmetically acceptable medium.

In other words, the invention relates to the use of one or more compounds of formula (I), as defined previously, as moisturizer, alone or as a mixture, especially in a composition comprising a physiologically acceptable medium, in particular a cosmetically acceptable medium.

Similarly, the invention relates to the use of said composition for moisturizing keratin materials, preferably the skin, and more particularly for treating dry skin.

The invention also relates to a composition comprising, in a physiologically acceptable medium, one or more compounds of formula (I) as defined previously and one or more additional moisturizing active agents, these additional moisturizing active agents being other than the compounds of formula (I).

Moreover, the invention also relates to novel compounds of formula (I) as defined hereinafter and also to the compositions containing them, in particular the compositions in a physiologically acceptable medium.

Another subject of the present invention relates to a cosmetic process for moisturizing keratin materials, in particular the skin, which consists in applying to a keratin material, preferably to the skin, one of the compositions as defined previously. Preferably, the keratin materials, such as the skin, are human keratin materials.

Other characteristics, subjects and advantages of the invention will emerge more clearly on reading the description and the examples that follow.

In the text hereinbelow, and unless otherwise indicated, the limits of a range of values are included within that range.

The expression "at least one" is equivalent to the expression "one or more".

For the purposes of the present invention, the term "physiologically acceptable medium" is intended to denote a medium that has no unpleasant odour or appearance, and that is entirely compatible with the topical administration route. In the present case in which the composition is intended for topical administration, i.e. by application to the surface of the keratin material under consideration, such a medium is considered in particular to be physiologically acceptable when it does not cause discomfort, such as stinging or tautness that is unacceptable to the user.

In the present invention, the term "keratin material" means a keratin material, preferably a human keratin material, and in particular the skin (preferably human skin), and even more particularly bodily and/or facial skin.

The cutaneous region may be chosen in particular from:
the hands,
the face, in particular the forehead, the cheeks or the contour of an eye (periocular), and in particular the crow's feet, the region below the eye (bag), or the eyelids,
the neck,
the feet,
the legs,
the arms and forearms.

For the purposes of the present invention and unless otherwise indicated:
the saturated or unsaturated and optionally fused rings may also be optionally substituted;
the "alkyl" radicals are saturated, linear or branched, generally $C_1$-$C_{18}$, particularly $C_1$-$C_{10}$, hydrocarbon-based radicals, preferably $C_1$-$C_6$ alkyl radicals; as $C_1$-$C_{14}$ alkyl group, mention may in particular be made of methyl, ethyl, isopropyl, n-propyl, n-butyl, t-butyl, isobutyl, sec-butyl, pentyl, isopentyl, neopentyl, n-hexyl, n-heptyl and octyl groups;

the "alkenyl" radicals are linear or branched, unsaturated $C_2$-$C_{18}$ hydrocarbon-based radicals; preferably comprising one or more conjugated or unconjugated double bonds, such as ethylene, propylene, butylene, pentylene, 2-methylpropylene, prenyl and decylene;

the "alkynyl" radicals are linear or branched, unsaturated $C_2$-$C_{18}$ hydrocarbon-based radicals; preferably comprising one or more triple bonds;

the "aryl" radicals are fused or non-fused monocyclic or polycyclic carbon-based radicals, preferentially comprising from 6 to 30 carbon atoms, and of which at least one ring is aromatic; the aryl radical is preferentially chosen from a phenyl, biphenyl, naphthyl, indenyl, anthracenyl and tetrahydronaphthyl radical; the aryl radical is preferably a phenyl radical;

the "alkoxy" radicals are alkyloxy radicals with alkyl as defined above, the alkyl part of the alkoxy generally being $C_1$-$C_{18}$, preferably $C_1$-$C_{10}$, such as methoxy, ethoxy, propoxy and butoxy; when mention is made of unsaturated, this implies that the alkoxy group can represent an alkenyloxy or alkynyloxy group with alkenyl and alkynyl as defined above;

the "cycloalkyl" radicals are $C_4$-$C_8$ cycloalkyl radicals, preferably cyclopentyl and cyclohexyl radicals; the cycloalkyl radicals may be substituted cycloalkyl radicals, in particular substituted with alkyl, alkoxy, carboxylic acid, hydroxyl, amine and ketone groups;

the "heterocycloalkyl" radicals are saturated or partially unsaturated, nonaromatic heterocyclic radicals comprising from 4 to 8 ring members, which comprise from 1 to 3 heteroatoms, in particular chosen from oxygen, sulfur and nitrogen, preferably the morpholino, piperazino and piperidino radicals; the heterocycloalkyl radicals may be radicals which are substituted, in particular with alkyl, alkoxy, carboxylic acid, hydroxyl, amine and ketone groups;

the "aryl" or "heteroaryl" radicals can be substituted with at least one atom or group borne by at least one carbon atom, chosen from:

i) ($C_1$-$C_{10}$)alkyl, preferably $C_1$-$C_8$ alkyl, optionally substituted with one or more radicals chosen from the following radicals: hydroxyl, optionally unsaturated ($C_1$-$C_4$)alkoxy, (poly)hydroxy($C_2$-$C_4$)alkoxy, acylamino, amino substituted with two identical or different $C_1$-$C_4$ alkyl radicals optionally bearing at least one hydroxyl group or it being possible for the two radicals to form, with the nitrogen atom to which they are attached, a saturated or unsaturated and optionally substituted 5- to 7-membered, preferably 5- or 6-membered, heterocycle optionally comprising another nitrogen or non-nitrogen heteroatom; ii) halogen; iii) hydroxyl; iv) $C_1$-$C_4$ alkoxy; v) $C_1$-$C_{10}$ alkoxycarbonyl; vi) (poly)hydroxy($C_2$-$C_4$)alkoxy; vii) $C_2$-$C_4$ alkylcarbonyloxy, preferentially —O-acetyl or acetyloxy; viii) 5- or 6-membered heterocycloalkyl; ix) 5- or 6-membered heteroaryl, optionally substituted with a ($C_1$-$C_4$)alkyl radical, preferentially methyl; x) amino substituted with one or two identical or different $C_1$-$C_6$ alkyl radicals optionally bearing at least: a) one hydroxyl group, b) one amino group optionally substituted with one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other nitrogen or non-nitrogen heteroatom, c) one quaternary ammonium group —$N^+R'R''R'''$, a for which R', R" and R''', which may be identical or different, represent a hydrogen atom or a $C_1$-$C_4$ alkyl group; and $Q^-$ represents the anionic counterion such as the halide, d) one 5- or 6-membered heteroaryl radical, optionally substituted with a ($C_1$-$C_4$)alkyl radical, preferentially methyl; xi) acylamino (—N(R)—C(O)—R') in which the radical R is a hydrogen atom or a $C_1$-$C_4$ alkyl radical optionally bearing at least one hydroxyl group and the radical R' is a $C_1$-$C_2$ alkyl radical; xii) carbamoyl (($R)_2$N—C(O)—) in which the R radicals, which may be identical or different, represent a hydrogen atom or a $C_1$-$C_4$ alkyl radical optionally bearing at least one hydroxyl group; xiii) alkylsulfonylamino (R'S(O)$_2$—N(R)—) in which the radical R represents a hydrogen atom or a $C_1$-$C_4$ alkyl radical optionally bearing at least one hydroxyl group and the radical R' represents a $C_1$-$C_4$ alkyl radical or a phenyl radical; xiv) aminosulfonyl (($R)_2$N—S(O)$_2$—) in which the radicals R, which may be identical or different, represent a hydrogen atom or a $C_1$-$C_4$ alkyl radical optionally bearing at least one hydroxyl group; xv) carboxyl in the acid or salified form (preferably salified with an alkali metal or a substituted or unsubstituted ammonium); xvi) cyano; xvii) benzyloxycarbonyl; xviii) polyhaloalkyl, preferentially trifluoromethyl; xix) a phenylcarbonyloxy group optionally substituted with one or more hydroxyl groups; and xx) a phenyl group optionally substituted with one or more hydroxyl groups;

the "heteroaryl" radicals are radicals comprising, in at least one ring, one or more heteroatoms chosen in particular from O, N and S, preferably O or N, optionally substituted in particular with one or more alkyl, alkoxy, carboxyl, hydroxyl, amine or ketone groups, and at least one ring of which is aromatic. These rings may comprise one or more oxo groups on the carbon atoms of the heteroaryl; mention may in particular be made, among the heterocyclic radicals that may be used, of furyl, pyranyl, pyrrolyl, imidazolyl, pyrazolyl, pyridyl, thienyl, and pyrimidinyl groups; optionally, the heterocyclic groups are fused groups, such as benzofuranyl, chromenyl, xanthenyl, indolyl, isoindolyl, quinolyl, isoquinolyl, chromanyl, isochromanyl, indolinyl, isoindolinyl, coumarinyl or isocoumarinyl groups, it being possible for these groups to be substituted, in particular with one or more OH groups;

the "protective group" or "PG" of the "hydroxyl" or "amino" function is known by those skilled in the art; mention may be made of the two books "*Protective Groups in Organic Synthesis*", T. W. Greene, published by John Wiley & Sons, NY, 1981, pp. 193-217; "*Protecting Groups*", P. Kocienski, Thieme, 3rd ed., 2005.

In particular, the protective group is chosen from:

($C_1$-$C_6$)alkyl(thio)carbonyl such as formyl, acetyl or t-butylcarbonyl;

(di)(tri)halo($C_1$-$C_6$)alkyl(thio)carbonyl such as trifluoroacetyl (TFA);

($C_1$-$C_6$)alkoxy(thio)carbonyl such as methoxycarbonyl, ethoxycarbonyl, isobutyloxycarbonyl, t-butyloxycarbonyl (BOC), vinyloxycarbonyl, allyloxycarbonyl;

(di)(tri)halo($C_1$-$C_6$)alkoxy(thio)carbonyl such as 2,2,2-trichloroethylcarbonyl;

($C_1$-$C_6$)alkylthiothiocarbonyl;

(di)(tri)halo($C_1$-$C_6$)alkylthiothiocarbonyl;

(di)($C_1$-$C_6$)(alkyl)aminocarbonyl;

(di)($C_1$-$C_6$)(alkyl)aminothiocarbonyl;

optionally substituted arylcarbonyl such as phenylcarbonyl or 2,4,6-trimethylphenylcarbonyl;

optionally substituted aryloxycarbonyl such as p-nitrophenoxycarbonyl;

optionally substituted aryl($C_1$-$C_6$)alkoxycarbonyl such as benzyloxycarbonyl or Cbz, p-methoxybenzyloxycarbonyl, 3,4-d imethoxybenzyloxycarbonyl, o-nitrobenzyloxycarbonyl, p-nitrobenzyloxycarbonyl, 2-bromobenzyloxycarbonyl (2-bromo-Z) and 2-chlorobenzyloxycarbonyl (2-chloro-Z), 4-nitrobenzyloxycarbonyl (nitro-Z), heteroaryl($C_1$-$C_6$)alkoxycarbonyl such as 9-fluorenylmethoxycarbonyl (FMOC) or nicotinoyl;

(di)($C_1$-$C_6$)(alkyl)aminocarbonyl such as dimethylaminocarbonyl;

($C_1$-$C_6$)(alkyl)arylaminocarbonyl;

carboxyl;

optionally substituted aryl such as phenyl, dibenzosuberyl or 1,3,5-cycloheptatrienyl;

optionally substituted heteroaryl; especially including the cationic or non-cationic heteroaryls comprising from 1 to 4 heteroatoms below:

i) 5-, 6- or 7-membered monocyclic groups such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl, imidazolium;

ii) 8- to 11-membered bicyclic groups such as indolyl, indolinium, benzimidazolyl, benzimidazolium, benzoxazolyl, benzoxazolium, dihydrobenzoxazolinyl, benzothiazolyl, benzothiazolium, pyridoimidazolyl, pyridoimidazolium, thienocycloheptadienyl, these monocyclic or bicyclic groups being optionally substituted with one or more groups such as ($C_1$-$C_4$)alkyl, for instance methyl, or polyhalo($C_1$-$C_4$)alkyl, for instance trifluoromethyl;

iii) or the following tricyclic <u>ABC</u> group:

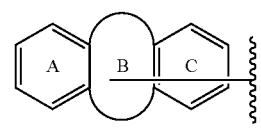

in which the two rings <u>A</u> and <u>C</u> optionally comprise a heteroatom, and ring <u>B</u> is a 5-, 6- or 7-membered ring, particularly a 6-membered ring, and contains at least one heteroatom, for instance piperidyl or pyranyl;

optionally cationic, optionally substituted heterocycloalkyl, the heterocycloalkyl group in particular representing a saturated or partially saturated 5-, 6- or 7-membered monocyclic group comprising from 1 to 4 heteroatoms chosen from oxygen, sulfur and nitrogen, such as di/tetrahydrofuranyl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidyl, morpholinyl, di/tetra/hexahydroazepinyl, di/tetrahydropyrimidinyl, these groups being optionally substituted with one or more groups such as ($C_1$-$C_4$)alkyl, oxo or thioxo, preferably tetrahydropyranyl THP; or the heterocycle represents the following group:

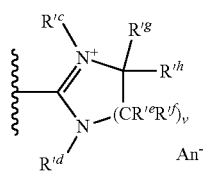

in which $R^{lc}$, $R^{ld}$, $R^{le}$, $R^{lf}$, $R^{lg}$ and $R^{lh}$, which may be identical or different, represent a hydrogen atom or a $(C_1\text{-}C_4)$alkyl group, or alternatively two groups $R^{lg}$ with $R^{lh}$, and/or $R^{le}$ with $R^{lf}$ form an oxo or thioxo group, or alternatively $R^{lg}$ with $R^{le}$ together form a cycloalkyl; and v represents an integer between 1 and 3 inclusive; preferentially, $R^{lc}$ to $R^{lh}$ represent a hydrogen atom; and $An^-$ represents a counterion;

isothiouronium —$C(NR^{lc}R^{ld})$=$N^+R^{le}R^{lf}$; $An^-$ with $R^{lc}$, $R^{ld}$, $R^{le}$ and $R^{lf}$, which may be identical or different, representing a hydrogen atom or a $(C_1\text{-}C_4)$alkyl group; preferentially, $R^{lc}$ to $R^{lf}$ represent a hydrogen atom; and $An^-$ represents a counterion;

isothiourea —$C(NR^{lc}R^{ld})$=$NR^{le}$; with $R^{lc}$, $R^{ld}$ and $R^{le}$ as defined above;

optionally substituted (di)aryl$(C_1\text{-}C_4)$alkyl or triaryl$(C_1\text{-}C_4)$alkyl such as 9-anthracenylmethyl, phenylmethyl (benzyl), diphenylmethyl or triphenylmethyl optionally substituted with one or more groups, in particular chosen from halogen, $(C_1\text{-}C_4)$alkyl, $(C_1\text{-}C_4)$alkoxy such as methoxy, hydroxyl, $(C_1\text{-}C_4)$alkylcarbonyl, (di)$(C_1\text{-}C_4)$(alkyl)amino such as dimethylamino, nitro;

optionally substituted (di)heteroaryl$(C_1\text{-}C_4)$alkyl or triheteroaryl$(C_1\text{-}C_4)$alkyl, the heteroaryl group in particular being cationic or noncationic, 5- or 6-membered monocyclic comprising from 1 to 4 heteroatoms chosen from nitrogen, oxygen and sulfur, such as pyrrolyl, furanyl, thiophenyl, pyridyl, pyridyl N-oxide such as 4-pyridyl or 2-pyridyl-N-oxide, pyrylium, pyridinium or triazinyl groups, optionally substituted with one or more groups such as alkyl, particularly methyl; advantageously, the (di)heteroaryl$(C_1\text{-}C_4)$alkyl is (di)heteroarylmethyl or (di)heteroarylethyl;

$CR^1R^1R^2R^3$ with $R^1$, $R^2$ and $R^3$, which may be identical or different, representing a halogen atom, such as (tri)(di)halo$(C_1\text{-}C_4)$alkyl such as 2,2,2-trichloroethyl or a group chosen from:

$(C_1\text{-}C_4)$alkyl such as methyl;
$(C_1\text{-}C_4)$alkoxy;
optionally substituted aryl such as phenyl optionally substituted with one or more groups, for instance $(C_1\text{-}C_4)$alkyl, $(C_1\text{-}C_4)$alkoxy or hydroxyl;
optionally substituted heteroaryl such as thiophenyl, furanyl, pyrrolyl, pyranyl or pyridyl, optionally substituted with a $(C_1\text{-}C_4)$alkyl group;
$P(Z^1)R^{l1}R^{l2}R^{l3}$ with $R^{l1}$ and $R^{l2}$, which may be identical or different, representing a hydroxyl, $(C_1\text{-}C_4)$alkoxy or alkyl group, $R^{l3}$ representing a hydroxyl or $(C_1\text{-}C_4)$alkoxy group, and $Z^1$ representing an oxygen or sulfur atom;
$(C_2\text{-}C_6)$alkylene, in particular allyl $H_2C$=$CH$—$CH_2$—;
optionally substituted arylsulfonyl such as p-toluenesulfonyl (Tos);
sterically hindered cycloalkyl such as the adamantyl group;
sterically hindered cycloalkyloxy(thio)carbonyl such as 1-adamantyloxycarbonyl (Adoc) or 1-(adamantyl)-1-methylethoxycarbonyl (Adpoc);

optionally substituted $(C_1\text{-}C_4)$alkoxy$(C_1\text{-}C_4)$alkyl such as methoxymethyl (MOM), ethoxyethyl (EOM) and isobutoxymethyl;
(tri)(di)halo$(C_1\text{-}C_4)$alkyl such as 2,2,2-trichloroethyl;
$R_eR_fR_gSi$— with $R_e$, $R_f$ and $R_g$, which may be identical or different, representing a $(C_1\text{-}C_6)$alkyl group, optionally substituted aryl group, optionally substituted (di)aryl$(C_1\text{-}C_4)$alkyl group, optionally substituted triaryl$(C_1\text{-}C_4)$alkyl group, such as benzyl, in particular chosen from trimethylsilyl or TMS, triethylsilyl, isopropyldimethylsilyl, tert-butyldimethylsilyl or TBDMS, (triphenylmethyl)dimethylsilyl, t-butyldiphenylsilyl, methyldiisopropylsilyl, methyl(di-t-butyl)silyl, tribenzylsilyl, tri-p-xylylsilyl, triisopropylsilyl, triphenylsilyl;
or else two contiguous hydroxyl groups can be protected with an alkylene group *—$C(R^j)(R^m)$—$(C(R^k)(R^l))_g$—* as drawn below:

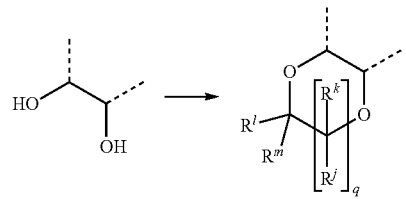

with $R^j$, $R^k$, $R^l$, and $R^m$, which may be identical or different, representing a hydrogen atom or a $(C_1\text{-}C_4)$alkyl, (poly)halo$(C_1\text{-}C_4)$alkyl, optionally substituted aryl such as phenyl, aryl$(C_1\text{-}C_4)$alkyl such as benzyl, (poly)halo$(C_1\text{-}C_4)$alkoxy, $(C_1\text{-}C_4)$alkoxy, halogen, (di)$(C_1\text{-}C_4)$(alkyl)amino or hydroxyl group, or else two $R^j$ and $R^k$ and/or $R^l$, and $R^m$ groups form, together with the carbon atom which bears them, an oxo group or a (hetero)cycloalkyl group such as cyclohexyl or cyclopropyl; q is 0, 1, 2 or 3, preferably *—$C(R^j)(R^m)$—$(C(R^k)(R^l))_q$—* represents a methylene, ethylene, propylene, dimethylmethylene, *—$C(CH_3)_2$—* or diphenylmethylene *—$C(Ph)_2$-*, cyclopentylidene, cyclohexylidene, cycloheptylidene, benzylidene, p-methoxybenzylidene, 2,4-dimethoxybenzylidene, methoxymethylene and ethoxymethylene;

the term "hydrogen peroxide-generating system" is intended to mean a chemical compound which is not $H_2O_2$ but which can generate hydrogen peroxide and/or which contains hydrogen peroxide, such as a) urea peroxide; b) polymeric complexes that can release hydrogen peroxide, such as polyvinylpyrrolidone/$H_2O_2$, in particular which is in the form of powders, and the other polymeric complexes described in U.S. Pat. Nos. 5,008,093, 3,376,110 and 5,183,901; c) oxidases in the presence of an appropriate substrate (for example glucose in the case of glucose oxidase or uric acid with uricase); d) metal peroxides which, in water, generate hydrogen peroxide, such as calcium peroxide or magnesium peroxide; e) perborates; or f) percarbonates; in particular, they are chosen from a) urea peroxide; b) polymeric complexes that can release hydrogen peroxide, chosen from polyvinylpyrrolidone/$H_2O_2$; c) oxidases; e) perborates and f) percarbonates.

I. 5-Oxazolidine-2,4-Dione C-Glycoside Derivatives

The 5-oxazolidine-2,4-dione C-glycoside derivatives in accordance with the present invention correspond to formula (I) below, and also the solvates thereof such as hydrates, the optical and geometric isomers and tautomers thereof and the organic or mineral base or acid salts thereof,

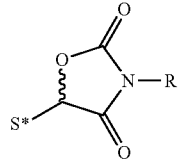

(I)

in which formula (I):
S* denotes a monosaccharide sugar radical or denotes a polysaccharide sugar radical comprising from 2 to 5 saccharide units, each saccharide unit (the saccharide unit in the case of a monosaccharide or each saccharide unit in the case of polysaccharides) comprising one or more hydroxyl groups optionally substituted with a radical R' chosen from:
i) $(C_1-C_6)$alkyl or $(C_2-C_6)$alkenyl; or
ii) an acetyl radical; or
iii) a protective group (PG) for hydroxyl function(s), such as $(C_2-C_6)$alkyl(thio)carbonyl or benzyl;
said monosaccharide radical possibly also being deoxygenated in position 2 (on its $C_2$ carbon atom);
said monosaccharide or polysaccharide radical possibly also comprising one or more amino groups $NR_bR_c$ with $R_b$ and $R_c$, which may be identical or different, representing a hydrogen atom, or an acetyl group, or a protective group for the amino function, such as $(C_2-C_6)$alkyl(thio)carbonyl;
said monosaccharide or polysaccharide radical being connected to the rest of the molecule by a bond between the $C_1$ carbon atom of one of the sugars of said monosaccharide or polysaccharide radical, this bond possibly being α or β anomeric;
R represents
i) a hydrogen atom;
ii) a $(C_1-C_{18})$alkyl group;
iii) an aryl$(C_1-C_4)$alkyl group optionally substituted with at least one hydroxyl and/or $(C_1-C_4)$alkoxy group, such as benzyl;
iv) a cycloalkyl group.

Preferably, the hydroxyl radicals of the radical S* are not substituted or are all substituted with the same group R' as previously defined, in particular with an acetyl group. Preferably, the optional amino group(s) $NR_bR_c$ of the radical S* denote(s) $NHR_b$ with $R_b$ all denoting a hydrogen atom or all denoting an acetyl group.

More preferentially, the hydroxyl radicals of the radical S* are not substituted, and the optional amino group(s) $NR_bR_c$ of the radical S* denote(s) $NHR_b$ with $R_b$ all denoting a hydrogen atom or all denoting an acetyl group.

According to one preferred form of the invention, the hydroxyl radicals of the radical S* are not substituted, and the radical S* is not substituted with an amino radical $NR_bR_c$.

According to one advantageous embodiment, R represents
i) a hydrogen atom;
ii) a $(C_1-C_{18})$alkyl group, in particular a $(C_1-C_6)$alkyl group and more particularly a $(C_1-C_4)$alkyl group such as a methyl group.

It is understood that, for the compounds of formula (I) as defined above, when S* represents a monosaccharide radical, then it can be in pyranose form (the sugar heterocycle which constitutes it comprises 6 ring members) or furanose form (the sugar heterocycle which constitutes it comprises 5 ring members); and when S* represents a polysaccharide radical, it comprises the sequence of 2 to 5 saccharide units, which may be identical to or different from one another, which may be in furanose or pyranose form.

It is understood that, for the compounds of formula (I) as previously defined, when S* represents a polysaccharide radical, the polysaccharide is preferably a disaccharide which results from the linking of 2 pyranose units or the linking of one saccharide unit in furanose form and one unit in pyranose form or the linking of one saccharide unit in pyranose form and one unit in furanose form; whether it is for the monosaccharide or polysaccharide radical, each saccharide unit can possibly be in the laevorotatory L form or the dextrorotatory D form, and in α or β anomeric form.

According to one preferred embodiment, the sugar radical S* represents a monosaccharide radical in which the heterocycle constituting it contains 4 or 5 carbon atoms, of formula S*' below:

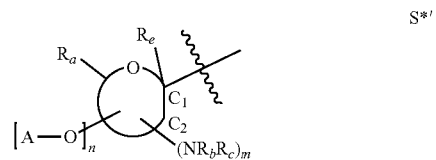

S*'

$R_a$ representing a hydrogen atom, a $(C_1-C_4)$alkyl group such as methyl or a (poly)hydroxy$(C_1-C_4)$alkyl group such as hydroxymethyl or 1,2-dihydroxyethyl, the hydroxyl function(s) of the (poly)hydroxy$(C_1-C_4)$alkyl group being substituted with A as defined below;
it being understood that the $R_a$ radical is in the $C_5$ position if the sugar unit is in pyranose form or in the $C_4$ position if it is in furanose form;
$R_b$ representing a hydrogen atom or a $(C_1-C_4)$alkyl group, preferably hydrogen;
$R_c$ representing a hydrogen atom, or a protective group for the amine function, such as $R_d$—C(X')—, identical in the case of several hydroxyl functions, with X' representing an oxygen or sulfur atom, in particular an oxygen atom, and $R_d$ representing a $(C_1-C_4)$alkyl group, $R_c$ preferably representing an acetyl group $CH_3$—C(O)—;
$R_e$ represents a hydrogen atom or a $CH_2$—O—A group;
A representing a hydrogen atom, a $(C_1-C_6)$alkyl group or a hydroxyl-function-protecting group, such as $R_d$—C(X')— as defined above and in particular acetyl $CH_3$—C(O)—, or else, when n is greater than or equal to 2 and two groups A-O are contiguous, then two A groups can together form a linear or branched $(C_1-C_6)$alkylene chain; preferably, when A is different from a hydrogen atom and from a $(C_1-C_6)$alkyl group, all the protective groups A are identical;
more preferentially, A represents a hydrogen atom;
n is equal to 1, 2 or 3 and m is equal to 0 or 1.
Preferably, m is 0.

According to another preferred embodiment, the sugar radical S* represents a polysaccharide radical constituted of 2 to 5 saccharide units, in particular of 2 to 3 and preferably of 2 saccharide units, linked together via an oxygen atom (oxy), 1→4 ($C_1$ of one saccharide unit →$C_4$ of the other saccharide unit) or 1→3 ($C_1$ of one saccharide unit →$C_3$ of the other saccharide unit) or 1→6 ($C_1$ of one saccharide unit →$C_6$ of the other saccharide unit), each saccharide unit of which is constituted of a heterocycle comprising 4 or 5 carbon atoms, of formula S*''' below:

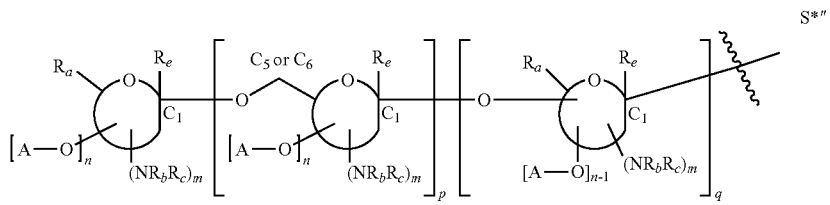

in which formula S*''', p and q represent integers inclusively between 0 and 4, with p+q inclusively between 1 and 4, particularly between 1 and 2, preferentially p+q=1; $R_a$, which may be identical or different, are as defined above, $R_b$, which may be identical or different, are as defined above, $R_c$, which may be identical or different, are as defined above, $R_e$, which may be identical or different, are as defined above, A, which may be identical or different, are as defined above, m, which may be identical or different, are as defined above, n, which may be identical or different, are as defined above, it being understood that the two sugar units between the square brackets q and p can be reversed, i.e. can represent the following sequence:

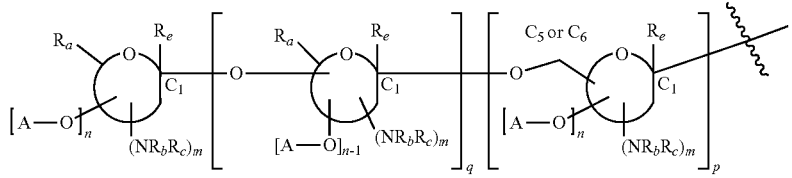

According to one preferred variant of the invention, the compounds of formula (I) are such that:

S* represents a monosaccharide sugar radical chosen from: glucose, galactose, mannose, xylose, lyxose, fucose, arabinose, rhamnose, quinovose, fructose, sorbose, talose, 2-deoxyglucose, N-acetylglucosamine, N-acetylgalactosamine, glucosamine, galactosamine; or a disaccharide chosen from: lactose, maltulose, palatinose, lactulose, amygdalose, turanose, cellobiose, isomaltose, rutinose, maltose; more preferentially, S* represents a monosaccharide sugar radical chosen from glucose, xylose, rhamnose, galactose or mannose; even more preferentially, S* represents a monosaccharide sugar radical chosen from glucose, xylose, rhamnose, galactose or mannose; even more preferentially, S* represents a monosaccharide sugar radical chosen from glucose, rhamnose or xylose, in particular glucose or xylose.

More preferentially, the compounds of formula (I) are chosen from the compounds of formulae (I'), (I''), (I''''), (I'a), (I''a) and (I''''a) below:

(I')

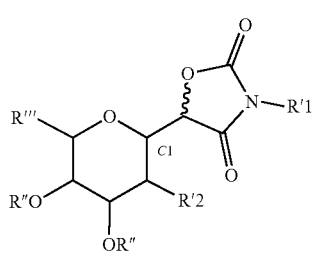

(I'a)

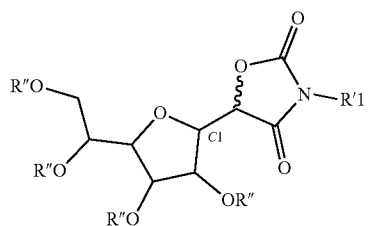

(I'')

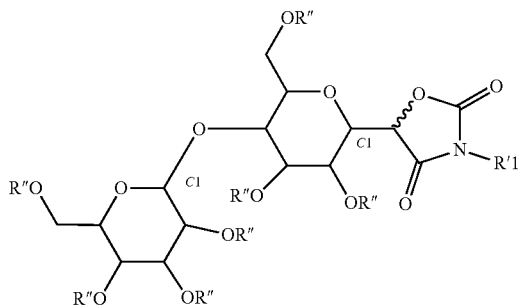

(I'''')

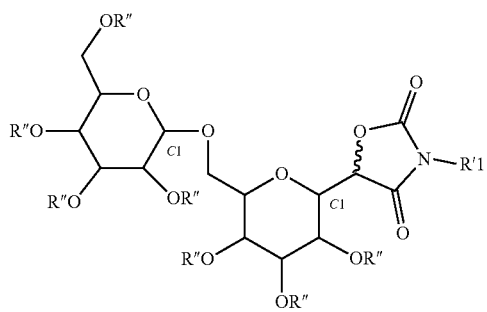

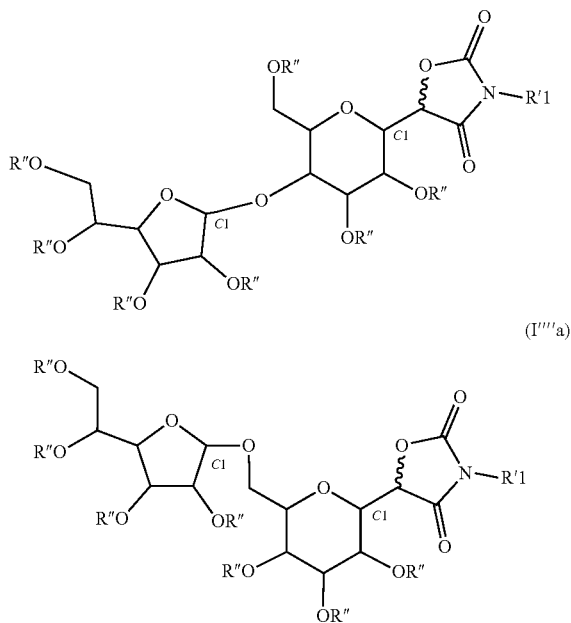

and also the solvates thereof such as hydrates, the optical and geometric isomers and tautomers thereof and the salts thereof, in which formulae (I'), (I''), (I'''), (I'a), (I''a) and (I''''a):
- R'$_1$ has the same definition as that of R for the compounds of formula (I); preferably, R'$_1$ represents a hydrogen atom; or a (C$_1$-C$_6$)alkyl, in particular (C$_1$-C$_4$)alkyl, radical, such as a methyl radical;
- R'$_2$ represents a hydrogen atom or the group —OR'' with R'' as defined below;
- R'' represents
  i) (C$_1$-C$_6$)alkyl; or
  ii) an acetyl radical; or
  iii) a protective group (PG) for hydroxyl function(s), such as (C$_2$-C$_6$)alkyl(thio)carbonyl or benzyl; or
  iv) a hydrogen atom;
  preferably, R'' represents a hydrogen atom or an acetyl radical, and more particularly a hydrogen atom;
- R''' represents a hydrogen atom, or a (C$_1$-C$_4$)alkyl group, or a —CH$_2$OR'' group with R'' as defined previously, in particular hydrogen or an acetyl radical, and preferably a hydrogen atom.

According to one particular embodiment, the compounds of the invention are of formula (I').

According to another particular embodiment of the invention, the compounds of the invention are of formula (I'').

According to another particular embodiment of the invention, the compounds of the invention are of formula (I''').

According to another particular embodiment of the invention, the compounds of the invention are of formula (I'a).

According to another particular embodiment of the invention, the compounds of the invention are of formula (I''a).

According to another particular embodiment of the invention, the compounds of the invention are of formula (I''''a).

According to one particular embodiment, S* and S*' represent a monosaccharide radical chosen from glucose, galactose, mannose, xylose, lyxose, fucose, arabinose, rhamnose, ribose, deoxyribose, quinovose, fructose, sorbose, talose, 2-deoxyglucose, threose, erythrose, N-acetylglucosamine, N-acetylgalactosamine, glucosamine and galactosamine; in particular, S* and S*' represent a monosaccharide radical chosen from glucose, xylose, rhamnose, galactose or mannose; even more particularly, S* and S*' represent a monosaccharide radical chosen from glucose, xylose or rhamnose; and even more particularly, S* and S*' represent a monosaccharide radical chosen from glucose or xylose.

In particular, S* and S*' represent a monosaccharide radical chosen from D-glucose, D-galactose, D-mannose, D-xylose, L-xylose, D-lyxose, L-lyxose, L-fucose, L-arabinose, D-arabinose, L-rhamnose, L-ribose, D-ribose, 2-deoxy-D-ribose, 2-deoxy-L-ribose, D-quinovose, D-fructose, L-sorbose, D-talose, 2-deoxy-D-glucose, D-threose, D-erythrose, L-threose, L-erythrose, N-acetyl-D-glucosamine, N-acetyl-D-galactosamine, D-glucosamine and D-galactosamine. Preferably, S* and S*' denote a monosaccharide radical chosen from D-glucose, D-galactose, D-mannose, D-xylose or L-rhamnose; in particular, S* and S*' represent a monosaccharide radical chosen from D-glucose, D-xylose or L-rhamnose, and more particularly a D-glucose or D-xylose radical.

According to another particular embodiment, S* and S*' represent a polysaccharide radical and in particular a disaccharide radical chosen from lactose, maltulose, palatinose, lactulose, amygdalose, turanose, cellobiose, isomaltose, rutinose and maltose.

According to one particular form of the invention, S* and S*' represent a polysaccharide radical, in particular a disaccharide radical chosen from lactose, maltose and cellobiose. In particular, S* and S*' represent a disaccharide radical chosen from D-lactose, D-maltose and D-cellobiose.

By way of examples of novel compounds of formula (I) or (I'), (I''), (I''''), (I'a), (I''a) and (I''''a) according to the invention, mention may be made of the compounds 1a, 2a, 3a and 4a, and 1 to 8, and also the isomers thereof and/or the solvates thereof and/or the salts thereof and/or the tautomers thereof:

| compound | structure |
|---|---|
| 1a | 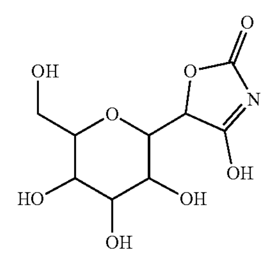 [SMILES: O=C1N=C(O)C(C2OC(CO)C(O)C(O)C2O)O1] |
| 2a | 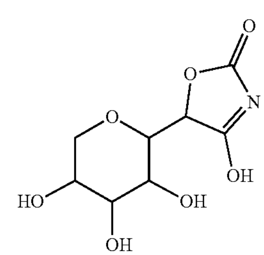 [SMILES: O=C1N=C(O)C(C2OCC(O)C(O)C2O)O1] |

-continued

| compound | structure |
|---|---|
| 3a | (structure: pyranose with CH2OH, 3 OH groups, attached to oxazolidinone with N-methyl) |
| 4a | (structure: methyl pyranose with 3 OH groups, attached to N-methyl oxazolidinone) |

| compound | sugar | structure |
|---|---|---|
| 1 | D-glucose | (structure) |
| 2 | D-xylose | (structure) |
| 3 | D-glucose | (structure) |

-continued

| compound | sugar | structure |
|---|---|---|
| 4 | L-rhamnose | (structure) |
| 5 | D-mannose | (structure) |
| 6 | D-mannose | (structure) |
| 7 | D-galactose | (structure, Chiral) |
| 8 | D-galactose | (structure) | and in particular the compounds 1, 2, 3, 4 and/or the solvates thereof and/or the salts thereof and/or the tautomers thereof.

The acceptable solvates of the compounds used in the present invention comprise conventional solvates such as those formed during the last step of the preparation of said compounds due to the presence of solvents. Mention may be made, by way of example, of the solvates due to the presence of water (hydrates) or of linear or branched alcohols, such as ethanol or isopropanol.

The salts of the compounds of formula (I) which comprise at least one amine function can be salts of an organic acid such as citric acid, lactic acid, tartaric acid, aspartic acid, glutamic acid, acetic acid, formic acid, trifluoroacetic acid, hydrochloric acid, glycolic acid or malic acid.

The salts of the compounds of formula (I) which comprise at least one acid function can also be chosen from metal salts, for example aluminium ($Al^{3+}$, zinc ($Zn^{2+}$), manganese ($Mn^{2+}$) or copper ($Cu^{2+}$); alkali metal salts, for example lithium ($Li^+$), sodium ($Na^+$) or potassium ($K^+$); or alkaline-earth metal salts, for example calcium ($Ca^{2+}$) or magnesium ($Mg^{2+}$). They can also be ammonium derivatives of formula $NH_4^+$ or organic salts such as ammoniums of formula $Y_3NH^+$, $NY_3$ denoting an organic amine, the Y radicals being identical or different, it being possible for two or three Y radicals to form, in pairs, a ring with the nitrogen atom which carries them or it being possible for $NY_3$ to denote an aromatic amine. The organic amines are for example alkylamines, for instance methylamine, dimethylamine, trimethylamine, triethylamine or ethylamine, or hydroxyalkylamines, for instance 2-hydroxyethylamine, bis(2-hydroxyethyl)amine or tris(2-hydroxyethyl)amine, or cycloalkylamines, for instance bicyclohexylamine or glucamine, piperidine, or pyridines and the like, for example collidine, quinine or quinoline, or amino acids which are basic in nature, for instance lysine or arginine.

In the case where the compounds according to the invention are in salt form, the anions or the cations are of course in an amount which ensures the electro-neutrality of the compounds of formula (I).

The salts of the compounds of formula (I) according to the invention which comprise at least one acid function can advantageously be chosen from the metal salts $Cu^{2+}$, $Mn^{2+}$ and $Zn^{2+}$, the alkali metal salts $Li^+$, $Na^+$ and $K^+$ and the alkaline-earth metal salts $Ca^{2+}$ and $Mg^{2+}$. According to another variant, the salts of the compounds of formula (I) according to the invention which comprise at least one acid function can advantageously be chosen from ammoniums, preferably from the salts of amino acids which are basic in nature, for instance lysine or arginine or from diethanolamine salts or triethanolamine salts.

II. Obtaining the 5-Oxazolidine-2,4-Dione C-Glycoside Compounds

1) Process for the synthesis of the novel compounds of formula (I)

The compounds of formula (I) may be obtained by the synthetic pathway described below:

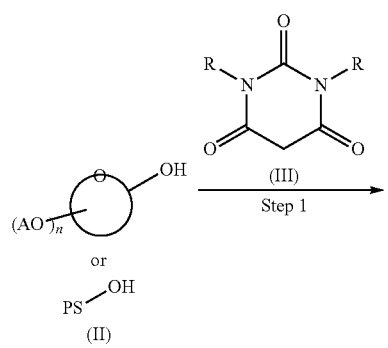

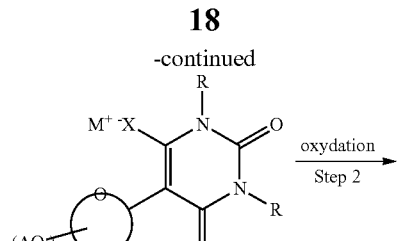

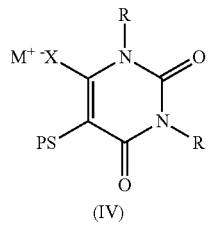

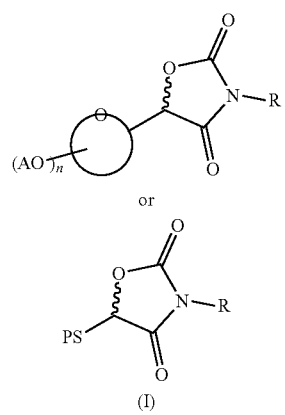

in which (II) denotes a monosaccharide represented by:

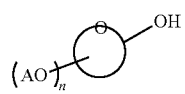

or a polysaccharide PS—OH, in which A, $R_a$, $R_b$, $R_c$, $R_e$, n, and m are as defined above, p' and q' representing an integer inclusively between 0 and 4, with p'+q' inclusively between 0 and 4, in particular between 0 and 2, preferably p'+q'=0 or 1, it being understood that the two units between square brackets can be reversed; PS—OH denoting a polysaccharide having the structure (gg) below:

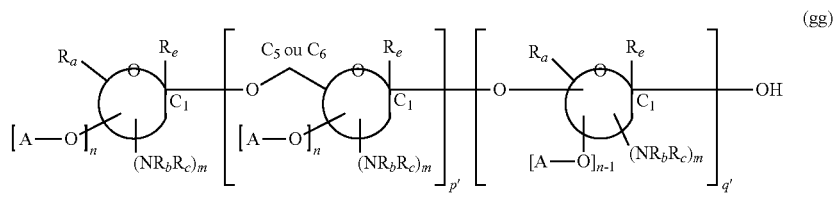

step 1 consisting in reacting a monosaccharide or a polysaccharide PS—OH of formula (II) with a barbituric acid derivative (III), in particular in the presence of a mineral base such as $M^+OH^-$, $M^+$ representing a cationic counterion or preferably a weak base such as (bi)carbonate, in particular with alkali metal (bi)carbonate, or in the presence of an organic base such as triethylamine or diisopropylethylamine;

in particular in a polar protic solvent such as water, by heating optionally at a temperature of between 30° C. and 100° C., in particular at 80° C., preferably for a period of between 1 hour and 24 hours, in particular between 3 hours and 10 hours, such as 5 hours, so as to give the compound comprising a sugar unit (IV);

step 2 consisting in reacting the compound (IV) with a chemical oxidizing agent such as hydrogen peroxide or a hydrogen peroxide-generating agent such as oxone or else a biological agent such as an enzyme of oxidase type, in particular in a polar solvent (or solvent mixture) with a boiling point of between 40° C. and 100° C. at atmospheric pressure, such as acetone or acetonitrile, or a polar protic solvent such as water, optionally in a basic medium and/or in the presence of a chelating agent such as ethylenediaminetetraacetic acid (EDTA) optionally in salt form, so as to give a C-glycoside compound (I) according to the invention, it being understood that, if A represents a hydrogen atom and it is desired to have a protective group PG, then a protection step is added, that, if $R_b$ and $R_c$ of $NR_bR_c$ optionally present on the monosaccharide or the polysaccharide (II) represent hydrogen atoms and it is desired to protect the amino group(s), a protection step is carried out, that, if the group R comprises a function sensitive to these synthesis steps, it will be advisable to add a protection/deprotection sequence.

Under certain reaction temperature and time conditions during step 2, it is possible to isolate the intermediate (V) according to step 2a:

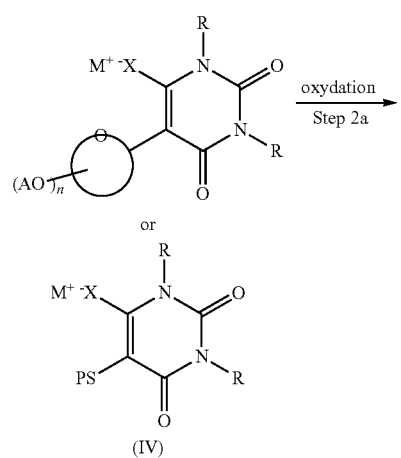

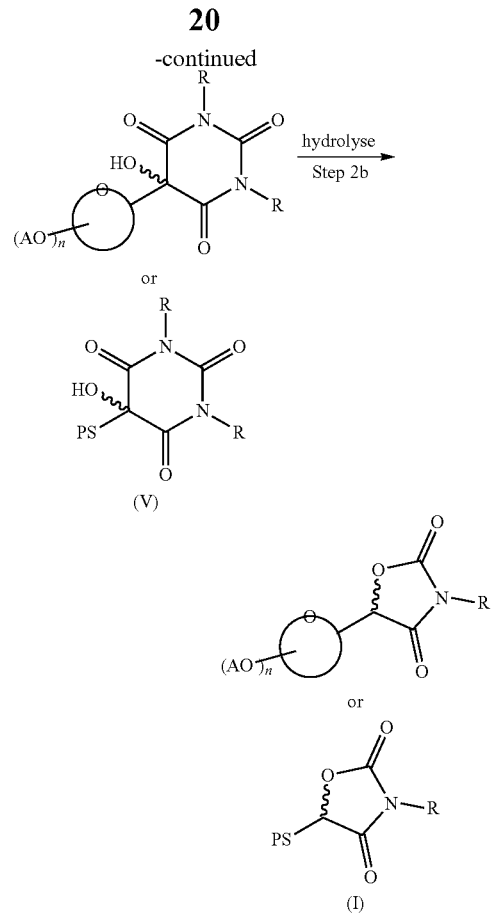

Step 2b consists in treating the compound (V) in a polar solvent (or solvent mixture) with a boiling point of between 40° C. and 100° C. at atmospheric pressure, such as acetone or acetonitrile, or a polar protic solvent such as water, optionally in a medium that is basic, in particular by addition of a mineral base such as sodium hydroxide or potassium hydroxide, and/or in the presence of a chelating agent such as ethylenediaminetetraacetic acid (EDTA) optionally in salt form, and optionally in the presence of a chemical oxidizing agent, such as hydrogen peroxide or a hydrogen peroxide-generating agent, such as oxone, or else a biological agent such as an enzyme of oxidase type, to give a C-glycoside compound (I) according to the invention.

The compounds of formula (V), and also the solvates and/or isomers and/or salts thereof, are novel. They can also be represented by the general formula below

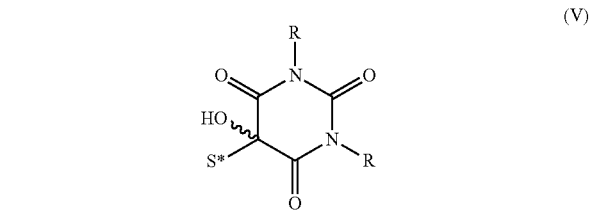

with S* and R as described above.

A subject of the invention is also the compounds of formula (V).

Thus, when the process described above uses D-glucose, it is possible to isolate, after step 1, then the oxidation step 2 carried out for a limited period of time, the novel compound 9 (and/or the solvates thereof and/or the salts thereof):

| compound | sugar | structure |
| --- | --- | --- |
| 9 | D-glucose | 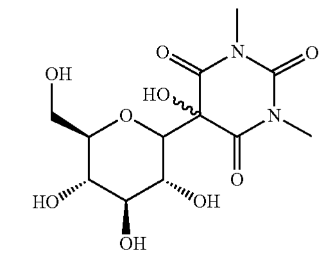 [SMILES: CN1C(=O)N(C)C(=O)C(O)(C2O[C@H](CO)[C@@H](O)[C@H](O)[C@H]2O)C1=O] |

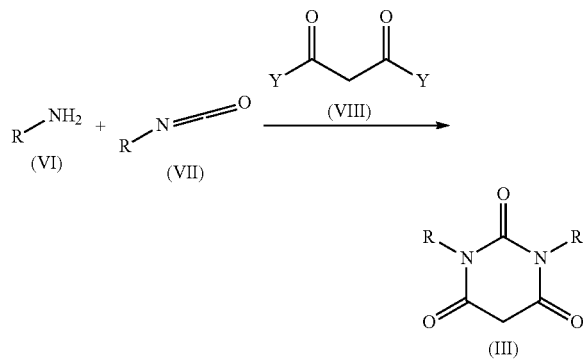

All the reagents are obtained by conventional methods known by those skilled in the art. In particular, the compounds (III) are commercially available or can be prepared, for example, by the following method:

$$R-NH_2 \;+\; R-N=C=O \;\;(VI)\;\;(VII)$$

$$Y\overset{O}{\underset{}{\parallel}}\!\!-\!\!\overset{O}{\underset{}{\parallel}}-Y \quad (VIII)$$

$$\text{(III)}$$

The amines (VI) are reacted with the isocyanates (VII) to form symmetrical urea, which then reacts with an activated malonyl derivative (VIII), such as malonyl chloride (Y=Cl), to give the compounds (III), the reaction being carried out in an aprotic polar solvent such as dichloromethane, THF, ether or acetonitrile, at temperatures ranging from 20° C. to 160° C.

Those skilled in the art will take care to protect or deprotect the sensitive functions according to the synthesis steps.

IV. Compositions

A subject of the invention is also a composition comprising, in particular in a physiologically acceptable medium, one or more compounds of formula (I), in particular one or more compounds of formula (I'), (I"), (I'''), (I'a), (I"a) and (I'''a), as defined previously.

In particular, a subject of the invention is also a composition comprising, in particular in a physiologically acceptable medium, one or more compounds from 1 to 8 as defined previously.

The compound(s) of formula (I) are preferably present in amounts ranging from 0.01% to 10% by weight, preferentially from 0.02% to 6% and even more particularly from 0.1% to 5% by weight, in particular from 2% to 7% by weight and more particularly from 3% to 6% by weight relative to the total weight of the composition.

As indicated previously, the invention also relates to a composition comprising one or more compounds of formula (I) or (I'), (I"), (I'''), (I'a), (I"a) and (I'''a) as defined previously and one or more additional moisturizing active agents other than the compounds of formula (I).

Preferably, the additional moisturizing active agents are chosen from glycerol, urea, hydroxyethylurea, hyaluronic acid, propanediol, trehalose, mannitol, xylitol, sorbitol, glycine, β-alanine, taurine, trimethylglycine, and polyethylene glycol (PEG) derivatives.

Another subject of the invention is a composition comprising, in a physiologically acceptable medium, one or more compounds chosen from compounds (1) to (8) and also the solvates thereof, the isomers thereof and/or the salts thereof, said composition possibly also containing one or more additional moisturizers as defined previously other than the compounds of formula (I) or (I'), (I"), (I'''), (I'a), (I"a) and (I'''a).

V. Treatment Process

The invention also relates to a cosmetic process for moisturizing keratin materials, in particular the skin, which consists in applying to a keratin material, preferably to the skin, one of the compositions as defined previously.

Preferably, the keratin materials, such as the skin, are human keratin materials.

More particularly, the present invention relates to a cosmetic process for moisturizing dry skin, characterized in that one of the compositions as defined previously is applied to dry skin.

More particularly, the process according to the invention is characterized in that said composition according to the invention comprising the compound(s) of formula (I) or (I'), (I"), (I'''), (I'a), (I"a) and (I'''a), preferably the compound(s) 1 to 8, is applied once or repeatedly one to two times per day, preferably once a day, preferably over a period of at least one week, and more particularly of at least four weeks.

The compound(s) of formula (I) according to the invention, or the compositions comprising them, may be used once or repeatedly one to two times per day, preferably once a day, preferably for at least one week, and more particularly for at least four weeks.

More particularly, the composition is applied to the keratin material, preferably the skin, i.e. to a cutaneous region chosen from:
  the hands,
  the face, in particular the forehead, the cheeks or the contour of an eye (periocular), and in particular the crow's feet, the region below the eye (bag), or the eyelids,
  the neck,
  the feet,
  the legs,
  the arms and forearms.

Presentation Forms

These compositions in which the compounds used according to the invention may be implemented are useful for the non-therapeutic care of the skin. They are in particular useful for moisturizing the skin, in particular for treating dry skin.

They may show their efficacy as non-therapeutic skin maintenance treatment, namely preventive treatment. They may also be used as non-therapeutic skin treatment after skin moisturization disorders have appeared.

A composition used according to the invention is advantageously suitable for topical application to the skin.

This composition may be a care composition, especially a dermatological composition. Preferably, it is a skincare composition.

For topical application to the skin, a composition according to the invention may be in any galenical form conventionally intended for this type of application and especially in the form of aqueous gels or aqueous or aqueous-alcoholic solutions. By adding a fatty or oily phase, they may also be in the form of dispersions of lotion type, emulsions of liquid or semi-liquid consistency of milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/W or O/W/O), microemulsions, vesicular dispersions of ionic and/or nonionic type, or wax/aqueous phase dispersions. These compositions are prepared according to the usual methods.

Aqueous Phase

The compositions according to the invention intended for cosmetic use may comprise at least one aqueous phase. They are in particular formulated as aqueous lotions or as water-in-oil or oil-in-water emulsions or as multiple emulsions (oil-in-water-in-oil or water-in-oil-in-water triple emulsions (such emulsions are known and described, for example, by C. Fox in "Cosmetics and Toiletries" —November 1986—Vol. 101—pages 101-112)).

The aqueous phase of said compositions contains water and generally other water-soluble or water-miscible solvents. The water-soluble or water-miscible solvents comprise short-chain, for example C1-C4, monoalcohols such as ethanol and isopropanol; diols or polyols.

The compositions according to the invention preferably have a pH ranging from 3 to 9, depending on the chosen support.

When the composition(s) are in emulsion form, they generally contain, depending on the nature of the emulsion, one or more emulsifying surfactants.

The total amount of emulsifiers will preferably be, in the composition(s) according to the invention, in active material contents ranging from 1% to 8% by weight and more particularly from 2% to 6% by weight relative to the total weight of the composition.

Fatty Phase

The compositions according to the invention may contain at least one water-immiscible organic liquid phase, known as a fatty phase. This phase generally comprises one or more hydrophobic compounds which render said phase water-immiscible. Said phase is liquid (in the absence of structuring agent) at ambient temperature (20-25° C.). Preferentially, the water-immiscible organic liquid phase in accordance with the invention generally comprises at least one volatile oil and/or non-volatile oil and optionally at least one structuring agent.

The term "oil" is understood to mean a fatty substance which is liquid at ambient temperature (25° C.) and atmospheric pressure (760 mmHg, i.e. $1.05 \times 10^5$ Pa). The oil can be volatile or non-volatile.

For the purposes of the invention, the term "volatile oil" means an oil that is capable of evaporating on contact with the keratin material, such as the skin, in less than one hour, at ambient temperature and atmospheric pressure. The volatile oils of the invention are volatile cosmetic oils, which are liquid at ambient temperature and which have a non-zero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg). The term "non-volatile oil" means an oil that remains on the keratin material, such as the skin, at ambient temperature and atmospheric pressure for at least several hours and that especially has a vapour pressure of less than $10^{-3}$ mmHg (0.13 Pa).

The oil can be chosen from any physiologically acceptable oil and especially cosmetically acceptable oil, in particular mineral, animal, plant or synthetic oils; especially volatile or non-volatile hydrocarbon and/or silicone and/or fluorinated oils and their mixtures.

More specifically, the term "hydrocarbon oil" is understood to mean an oil mainly comprising carbon and hydrogen atoms and optionally one or more functional groups chosen from hydroxyl, ester, ether or carboxyl functional groups. Generally, the oil exhibits a viscosity of 0.5 to 100 000 mPa·s, preferably of 50 to 50 000 mPa·s and more preferably of 100 to 300 000 mPa·s.

Mention may be made, as examples of volatile oil which can be used in the invention, of:
volatile hydrocarbon-based oils chosen from hydrocarbon-based oils containing from 8 to 16 carbon atoms, and especially $C_8$-$C_{16}$ isoalkanes of petroleum origin (also known as isoparaffins).

As examples of non-volatile oils that may be used in the invention, mention may be made of:
hydrocarbon-based plant oils such as liquid triglycerides of fatty acids of 4 to 24 carbon atoms, for instance caprylic/capric acid triglycerides such as those sold by the company Stéarineries Dubois or those sold under the names Miglyol 810, 812 and 818 by the company Dynamit Nobel, and jojoba oil,
linear or branched hydrocarbons of mineral or synthetic origin, such as liquid paraffins and their derivatives, liquid petrolatum, polydecenes, polybutenes, hydrogenated polyisobutene, such as Parleam, or squalane;
synthetic ethers containing from 10 to 40 carbon atoms;
synthetic esters such as isononyl isononanoate, isopropyl myristate, isopropyl palmitate or $C_{12}$ to $C_{15}$ alkyl benzoates;
silicone oils such as linear (dimethicone) or cyclic (cyclomethicone) non-volatile polydimethylsiloxanes (PDMSs).

The compositions according to the invention may also comprise one or more cosmetic adjuvants chosen from softeners, opacifiers, stabilizers, preserving agents, fragrances, a structuring agent for a fatty phase, in particular chosen from waxes, pasty compounds, gelling agents; organic or mineral fillers; thickeners or suspending agents, or any other ingredient normally used in cosmetics for this type of application.

Needless to say, a person skilled in the art will take care to select this or these optional additional compounds such that the advantageous properties intrinsically associated with the composition in accordance with the invention are not, or are not substantially, adversely affected by the envisaged addition(s).

The examples below illustrate the invention without, however, limiting the scope thereof.

EXAMPLES

A) Synthesis Examples

4.1 Synthesis of Compounds 1, 2, 3, 4 and 9

Example 1

Synthesis of Compound 1

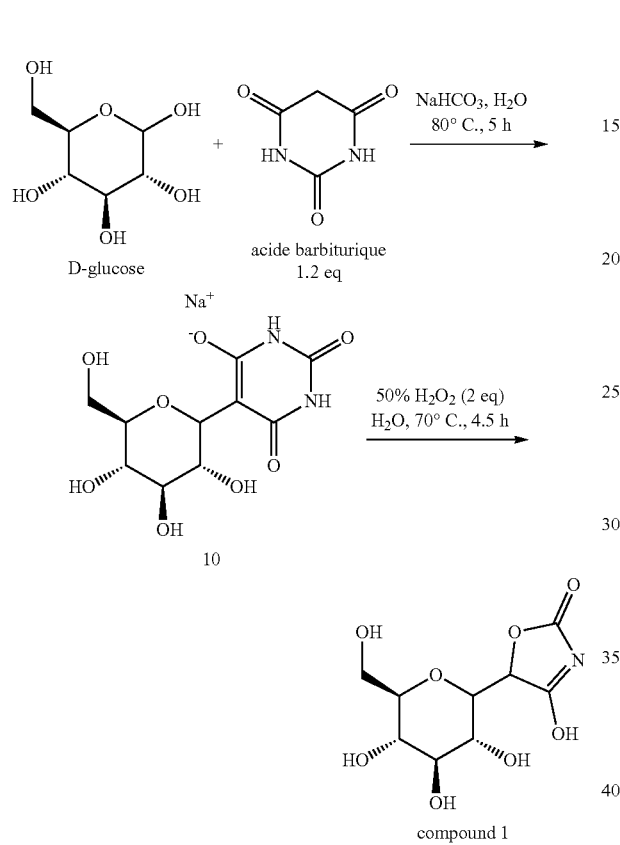

compound 1

Step 1. Barbituric acid (10.7 g, 83 mmol) is added, with stirring, to a solution of D-glucose (15 g, 83 mmol) in water (170 ml), then NaHCO$_3$ is added to pH 7. After neutralization, the mixture is heated at 80° C. for 5 h. The reaction is monitored by TLC in dichloromethane/MeOH 6:4+1% acetic acid. The reaction mixture is added dropwise to acetone (850 ml) with rigorous stirring. The precipitate obtained is filtered off and then washed 3 times in acetone, and the solid 10 obtained is dried under vacuum. It is isolated in the form of a yellow powder. The $^1$H NMR spectra and the mass spectrometry are in accordance with the expected structure.

Step 2. Hydrogen peroxide at 50% (137 mmol) is added, with stirring, to a solution of compound 10 (21.4 g, 68.5 mmol) in water (60 ml). The reaction mixture is brought to 70° C. for 4 h 30. The reaction is monitored by TLC (BuOH/H$_2$O/AcOH 6:2:2). The mixture is then added dropwise at ambient temperature to 600 ml of acetone. The residue formed is filtered off, then dissolved in water and the solution is concentrated to dryness. The powder obtained is washed twice in acetone, to give the compound 1 in the form of a pale yellow powder. The $^1$H NMR spectra and the mass spectrometry are in accordance with the expected structure.

Example 2

Synthesis of Compound 2

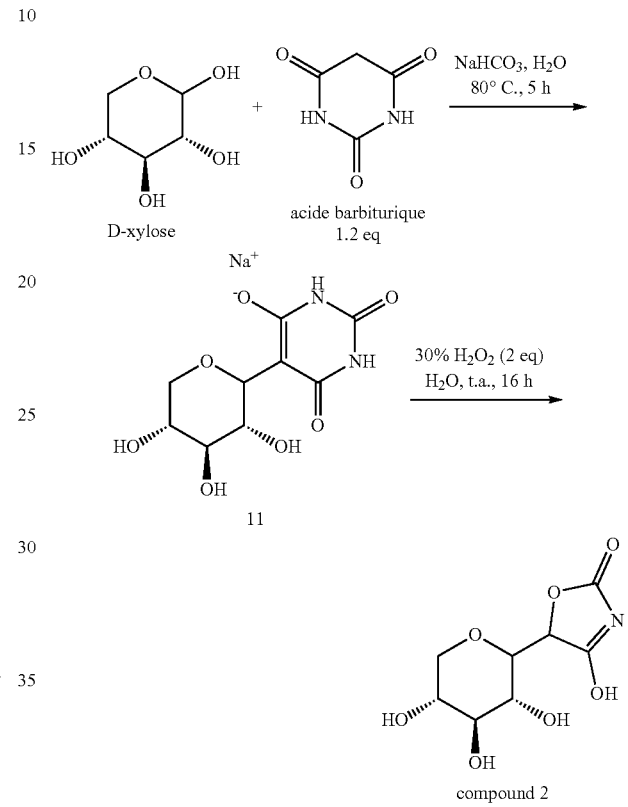

compound 2

Step 1. According to the process described in example 1, the intermediate 11 is obtained from D-xylose and barbituric acid. The $^1$H NMR spectra and the mass spectrometry are in accordance with the expected structure 11.

Step 2. 15 g of 11 (0.053 mol) in 35 ml of water were placed in a 100 ml three-necked round-bottomed flask equipped with a condenser, an argon inlet, a bubbler, a thermometer and a magnetic stirrer. 10.9 ml of 30% aqueous hydrogen peroxide in water (0.106 mol) were then added. The reaction medium is stirred at ambient temperature and the reaction is monitored by TLC with water/acetonitrile 8:2.

After stirring overnight, the starting product is consumed, but the peroxide test is positive. The reaction medium is heated at 80° C. for 3 hours (negative peroxide test), cooled to ambient temperature and then poured into a round-bottomed flask containing 250 ml of ethanol, before being concentrated to dryness in a rotary evaporator.

The paste obtained is taken up with acetone using a mortar, to give the compound 2 in the form of a light beige powder. The $^1$H NMR spectra and the mass spectrometry are in accordance with the expected structure.

Example 3

Synthesis of Compound 3

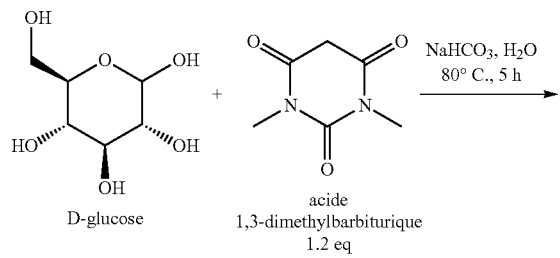

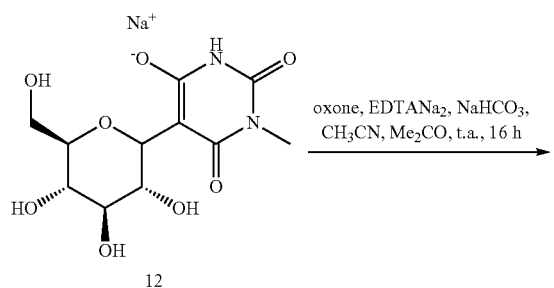

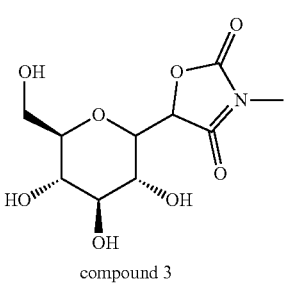

compound 3

Step 1. According to the process described in example 1, the intermediate 12 is obtained from D-glucose and 1,3-dimethylbarbituric acid. The $^1$H NMR spectra and the mass spectrometry are in accordance with the expected structure 12.

Step 2. An aqueous solution of Na$_2$EDTA (13 mg in 90 ml of water, C=4.10$^{-4}$ M, 0.036 mmol) is added, with stirring, to a solution of 12 (10.0 g, 32.0 mmol) in 140 ml of acetonitrile.

After a few minutes, the mixture is cooled in an ice bath and then 25 ml of acetone are added. An oxone (48.0 g, 78.1 mmol)/NaHCO$_3$ (20.0 g, 238 mmol) mixture is then slowly added. Stirring is continued overnight at ambient temperature, then the reaction mixture is filtered. After evaporation under vacuum, the residue is taken up in methanol, and the insoluble matter is filtered off. The filtrate is evaporated under vacuum and then purified on silica gel (dichloromethane/MeOH 8:2). The compound 3 is obtained in the form of a white solid. The $^1$H NMR spectra and the mass spectrometry are in accordance with the expected structure.

Example 4

Synthesis of Compound 4

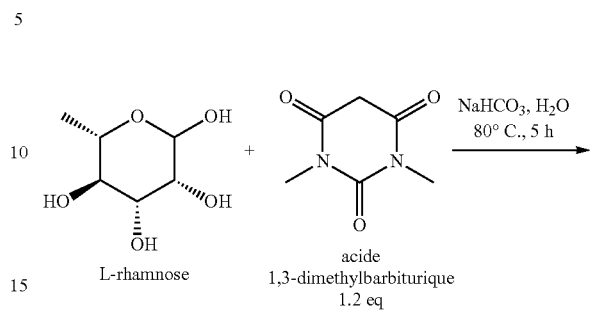

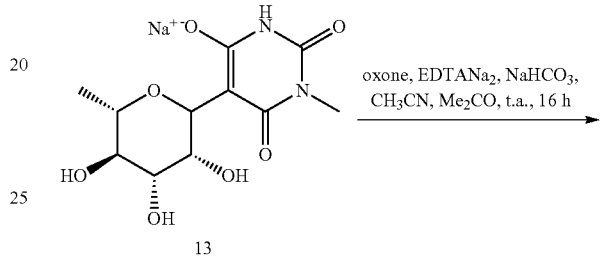

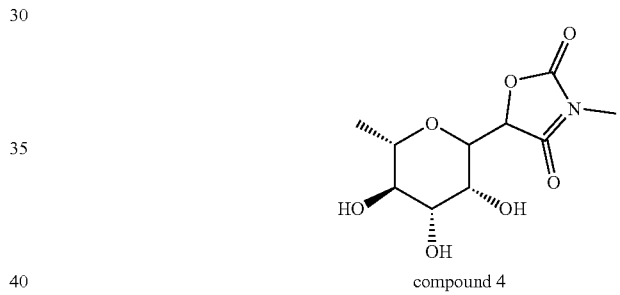

compound 4

Step 1. According to the process described in example 1, the intermediate 13 is obtained from L-rhamnose and 1,3-dimethylbarbituric acid. The $^1$H NMR spectra and the mass spectrometry are in accordance with the expected structure 13.

Step 2. An aqueous solution of Na$_2$EDTA (7 mg in 46 ml of water, 0.019 mmol) is added, with stirring, to a solution of 13 (5.0 g, 15.4 mmol) in 80 ml of acetonitrile. After a few minutes, the mixture is cooled in ice and then 13 ml of acetone are added. An oxone (25.2 g, 41.0 mmol)/NaHCO$_3$ (10.5 g, 125 mmol) mixture is then carefully added at a rate of approximately ⅔ of a spatula every 10 min. The pH is stabilized at approximately 7.3. Stirring is continued overnight at ambient temperature, then the reaction mixture is filtered. After evaporation under vacuum, the residue is purified on silica gel by elution with an increasing gradient of MeOH in dichloromethane. The compound 4 is obtained in the form of a yellow oil. The $^1$H NMR spectra and the mass spectrometry are in accordance with the expected structure.

Example 5

Synthesis of Compound 9

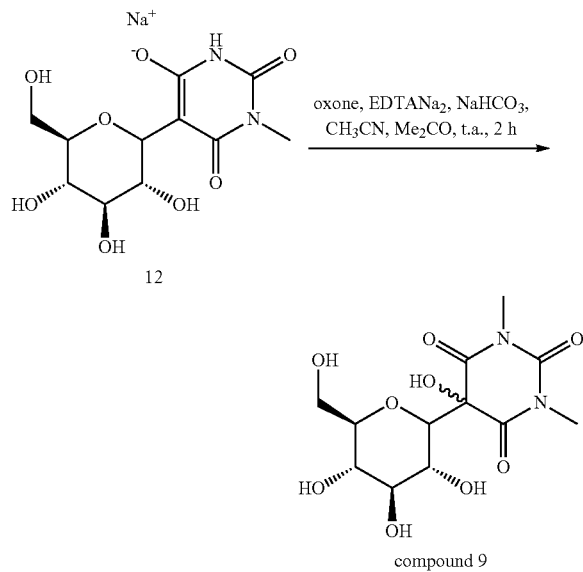

compound 9

An aqueous solution of Na$_2$EDTA (0.4 mM, 1 ml, 0.35 μmol) is added, with stirring, to a solution of 12 (100 mg, 0.294 mmol) in 1.5 ml of acetonitrile. After a few minutes, the mixture is cooled in ice and then 0.26 ml of acetone are added. An oxone (0.5 g, 0.814 mmol)/NaHCO$_3$ (0.2 g, 2.38 mmol) mixture is then carefully added all at once. The pH is stabilized at approximately 8. After 2 h of stirring, the reaction mixture is filtered and concentrated under vacuum in order to obtain 70 mg of compound 9 in the form of a white paste. The $^1$H NMR spectra and the mass spectrometry are in accordance with the expected structure 9.

B): Evaluation of the Moisturizing Potential on Isolated Stratum Corneum by Measurement with a Corneometer A test was performed to evaluate the moisturizing potential of the compounds of the invention formulated in an aqueous solution to an amount of 5% by weight relative to the total weight of the composition.

The technique makes it possible to measure the dielectric capacitance of the stratum corneum (SC), which depends on the mean dielectric permittivity value of the tissue. The dielectric permittivity varies greatly with the amount of water contained in the SC.

The SC samples are conditioned at 75% relative humidity and at 25° C. before/during the measurements and the treatment. The capacitance measurement is performed using a Corneometer™ (Courage & Khazaka, Germany).

The compound tested, compounds 1, 2 and 3 according to the invention or a moisturizing active agent such as glycerol (humectant positive control), is dissolved in a water/n-propanol mixture (80/20) and the solution is deposited onto the SC at a rate of 5 μl/cm$^2$ followed by air-drying for a total duration of 4 h.

A measurement is taken at T0h, before the treatment, and a measurement T4h is taken after total drying of the treatment.

The variation in the level of moisturization between T0h and T4h is calculated for each condition tested and compared to the references (carrier control and positive control) and to its T0h. The experiments are carried out on at least two different batches of SC and three samples of SC per condition tested.

The variation in the corneometer signal (HCM) after treatment is calculated for each SC sample: DHCMi=HCMi(T4h)−HCMi(T0h).

The results are then expressed as relative percentage in relation to the references, the carrier control and the glycerol positive control corresponding to a level of 0% and 100%, respectively.

Thus, for each experiment, the following are measured:

For the carrier control: DHCMi$_{carrier}$=HCMi$_{carrier}$(T4h)−HCMi$_{carrier}$(T0h)

For the positive control: DHCMi$_{glycerol}$=HCMi$_{glycerol}$(T4h)−HCMi$_{glycerol}$(T0h)

For the active agent: DHCMi$_{active\ agent}$=HCMi$_{active\ agent}$(T4h)−HCMi$_{active\ agent}$(T0h)

% DHCMi$_{active\ agent}$=(DHCMi$_{active\ agent}$−DHCMi$_{carrier}$)/((DHCMi$_{glycerol}$−DHCMi$_{carrier}$)

As specified above, according to this mode of calculation:
% DHCMi$_{carrier}$=0%
% DHCMi$_{glycerol}$=100%

The moisturizing potential of an active agent is therefore determined as relative percentage in relation to the positive control.

The mean of the relative percentages % DHCMi$_{active\ agent}$ are listed in the table below for compounds 1, 2 and 3 tested at 5%, compared to glycerol at 5%:

| Products tested in a water/n-propanol mixture | Mean DHCMi$_{active\ agent\ corr}$ |
| --- | --- |
| Carrier control | 0% |
| Glycerol at 5% by weight | 100% |
| Compound 1 according to the invention at 5% by weight | 88% |
| Compound 2 according to the invention at 5% by weight | 63% |
| Compound 3 according to the invention at 5% by weight | 51% |

It emerges from this test that the dielectric capacitance of the stratum corneum (SC) is high with compounds 1, 2 and 3 used according to the invention. In particular, the dielectric capacitance of the stratum corneum (SC) is of the same order with compound 1 used according to the invention in comparison with that obtained with glycerol at the same concentration.

C) Example 8

Skincare Cream

| | % by weight |
| --- | --- |
| Compound 1 | 4% |
| Glyceryl monostearate | 0.8% |
| Cetyl alcohol | 2.0% |
| Stearyl alcohol | 5.0% |
| Polyoxyethylene (20 OE) stearate | 3.0% |
| Crosslinked acrylic acid (Carbopol 941) | 0.3% |
| Caprylic/capric triglycerides | 12.0% |
| Preservatives | qs |
| Water qs | 100.0% |

When applied to the skin, the illustrated cosmetic formulation shows a good moisturizing effect on the skin.

The invention claimed is:
1. A process for moisturizing keratin material, which method comprises applying to the keratin material one or more 5-oxazolidine-2,4-dione C-glycoside derivatives corresponding to formula (I) below,
and also the solvates thereof, the optical and geometric isomers and tautomers thereof and the organic or mineral base or acid salts thereof,

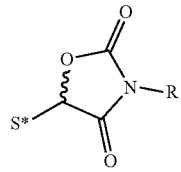

(I)

in which formula (I):
S* denotes a monosaccharide sugar radical or denotes a polysaccharide sugar radical comprising from 2 to 5 saccharide units, each saccharide unit (the saccharide unit in the case of a monosaccharide or each saccharide unit in the case of polysaccharides) comprising one or more hydroxyl groups optionally substituted with a radical R' chosen from:
i) ($C_1$-$C_6$)alkyl or ($C_2$-$C_6$)alkenyl; or
ii) an acetyl radical; or
iii) a protective group (PG) for hydroxyl function(s);
said monosaccharide radical possibly also being deoxygenated in position 2 (on its $C_2$ carbon atom);
said monosaccharide or polysaccharide radical possibly also comprising one or more amino groups $NR_bR_c$ with $R_b$ and $R_c$, which may be identical or different, representing a hydrogen atom, or an acetyl group, or a protective group for the amino function;
said monosaccharide or polysaccharide radical being connected to the rest of the molecule by a bond between the $C_1$ carbon atom of one of the sugars of said monosaccharide or polysaccharide radical, this bond possibly being α or β anomeric;
R represents
i) a hydrogen atom;
ii) a ($C_1$-$C_{18}$)alkyl group;
iii) an aryl($C_1$-$C_4$)alkyl group optionally substituted with at least one hydroxyl and/or ($C_1$-$C_4$)alkoxy group;
iv) a cycloalkyl group.

2. The process according to claim 1, in which the one or more 5-oxazolidine-2,4-dione C-glycoside derivatives corresponding to formula (I) comprise(s) a radical R chosen from:
i) a hydrogen atom;
ii) a ($C_1$-$C_{18}$)alkyl group.

3. The process according to claim 1, in which the one or more 5-oxazolidine-2,4-dione C-glycoside derivatives corresponding to formula (I) comprise(s) a sugar radical S* which represents a monosaccharide radical in which the heterocycle which forms it contains 4 or 5 carbon atoms, of formula S*' below:

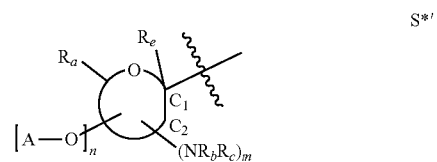

$R_a$ representing a hydrogen atom, a (C1-C4)alkyl group; or a (poly)hydroxy(C1-C4)alkyl group or the hydroxyl function(s) of the (poly)hydroxy(C1-C4)alkyl group being substituted with A, it being understood that the $R_a$ radical is in the $C_5$ position if the sugar unit is in pyranose form or in the $C_4$ position if it is in furanose form;
$R_b$ representing a hydrogen atom or a ($C_1$-$C_4$)alkyl group;
$R_c$ representing a hydrogen atom, or a protective group for the amine function;
$R_e$ represents a hydrogen atom or a —$CH_2$—O—A group;
A representing a hydrogen atom, a ($C_1$-$C_6$)alkyl group or a hydroxyl-function-protective group, or else, when n is greater than or equal to 2 and two groups A-O are contiguous, then two A groups can together form a linear or branched ($C_1$-$C_6$)alkylene chain; n is equal to 1, 2 or 3 and m is equal to 0 or 1.

4. The process according to claim 1, in which the one or more 5-oxazolidine-2,4-dione C-glycoside derivatives corresponding to formula (I) comprise(s) a sugar radical S* which represents a polysaccharide radical constituted of 2 to 5 saccharide units linked together via an oxygen atom (oxy), 1→4 ($C_1$ of one saccharide unit →$C_4$ of the other saccharide unit) or 1→3 ($C_1$ of one saccharide unit →$C_3$ of the other saccharide unit) or 1→6 ($C_1$ of one saccharide unit →$C_6$ of the other saccharide unit), each saccharide unit of which is constituted of a heterocycle comprising 4 or 5 carbon atoms, of formula S*'' below:

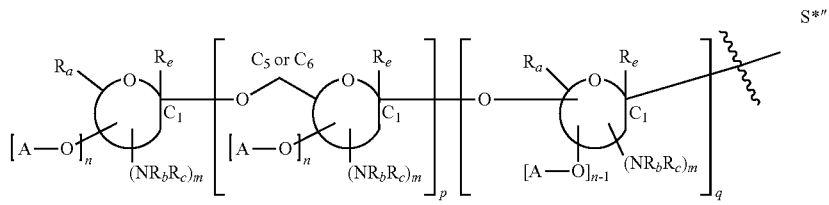

in which formula S*''':
Ra representing a hydrogen atom, a (C1-C4)alkyl group; or a (poly)hydroxy(C1-C4)alkyl group or the hydroxyl function(s) of the (poly)hydroxy(C1-C4)alkyl group being substituted with A, it being understood that the $R_a$ radical is in the $C_5$ position if the sugar unit is in pyranose form or in the $C_4$ position if it is in furanose form;

$R_b$ representing a hydrogen atom or a $(C_1-C_4)$alkyl group;

$R_c$ representing a hydrogen atom, or a protective group for the amine function;

$R_e$ represents a hydrogen atom or a —$CH_2$—O—A group;

A representing a hydrogen atom, a $(C_1-C_6)$alkyl group or a hydroxyl-function-protective group, or else, when n is greater than or equal to 2 and two groups A-O are contiguous, then two A groups can together form a linear or branched $(C_1-C_6)$alkylene chain; n is equal to 1, 2 or 3 and m is equal to 0 or 1;

p and q represent integers inclusively between 0 and 4, with p+q inclusively between 1 and 4, it being understood that the two sugar units between the square brackets q and p can be reversed, i.e. can represent the following sequence:

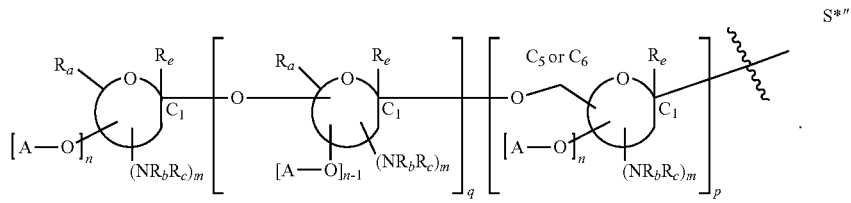

5. The process according to claim 1, in which the one or more 5-oxazolidine-2,4-dione C-glycoside derivatives corresponding to formula (I) comprise(s) a sugar radical S* which represents a monosaccharide radical chosen from glucose, galactose, mannose, xylose, lyxose, fucose, arabinose, rhamnose, ribose, deoxyribose, quinovose, fructose, sorbose, talose, 2-deoxyglucose, threose, erythrose, N-acetylglucosamine, N-acetylgalactosamine, glucosamine and galactosamine.

6. The process according to claim 1, in which the one or more 5-oxazolidine-2,4-dione C-glycoside derivatives corresponding to formula (I) comprise(s) a sugar radical S* which represents a monosaccharide radical chosen from glucose, xylose and rhamnose.

7. The process according to claim 1, in which the one or more 5-oxazolidine-2,4-dione C-glycoside derivatives corresponding to formula (I) comprise(s) a sugar radical S* which represents a polysaccharide radical.

8. The process according to claim 1, in which the one or more 5-oxazolidine-2,4-dione C-glycoside derivatives corresponding to formula (I) is (are) chosen from the compounds of formulae (I'), (I''), (I'''), (I'a), (I''a) and (I''''a) below:

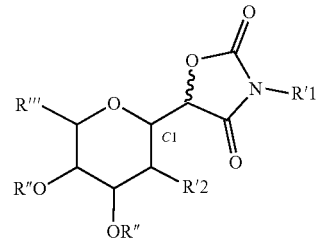
(I')

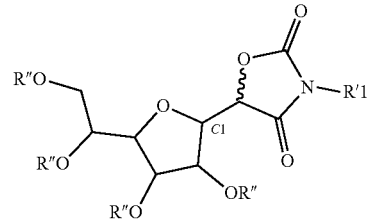
(I'a)

-continued

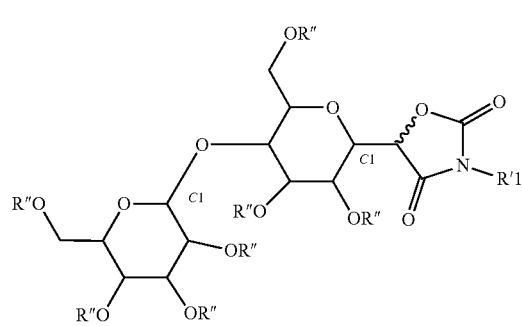
(I'')

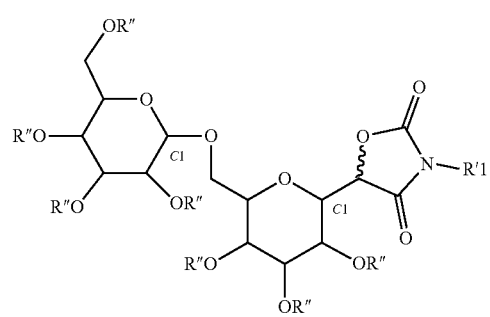
(I''')

(I″a)

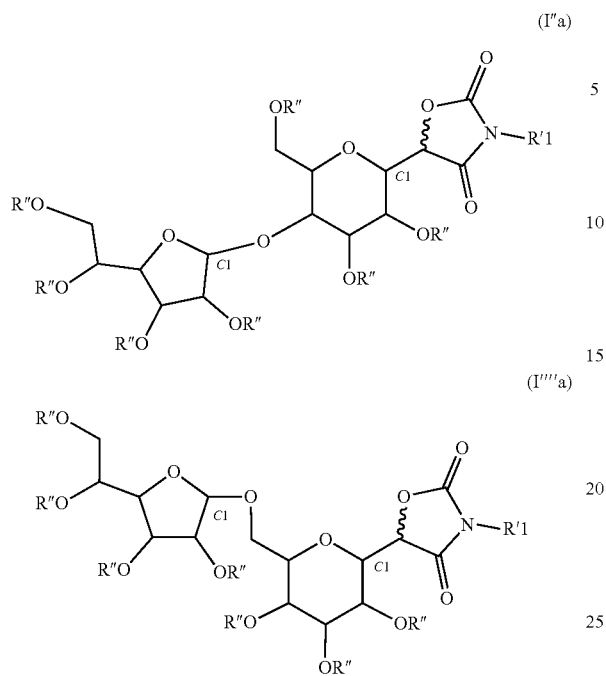

(I‴a)

and also the solvates thereof, the optical and geometric isomers and tautomers thereof and the salts thereof, in which formulae (I'), (I″), (I‴), (I'a), (I″a) and (I‴a):

$R'_1$ has the same definition as that of R for the compounds of formula (I);

$R'_2$ represents a hydrogen atom or the group —OR″ with R″;

R″ represents i) $(C_1-C_6)$alkyl; or ii) an acetyl radical; or iii) a protective group (PG) for hydroxyl function(s); or iv) a hydrogen atom;

R‴ represents a hydrogen atom, or a $(C_1-C_4)$alkyl group, or a —CH2—OR″ group with R″ as defined previously.

9. The process according to claim 1, in which the one or more 5-oxazolidine-2,4-dione C-glycoside derivatives corresponding to formula (I) are chosen from the following compounds:

| compound | structure |
|---|---|
| 1a | 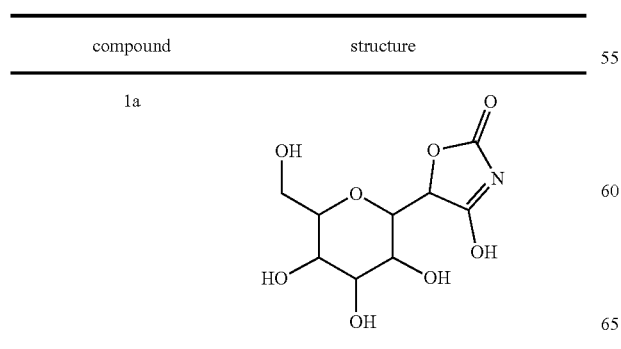 |

| compound | structure |
|---|---|
| 2a | 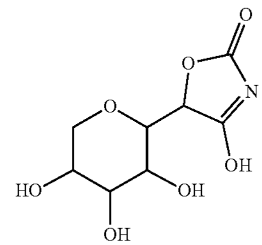 [SMILES: O=C1N=C(O)C(C2OCC(O)C(O)C2O)O1] |
| 3a | 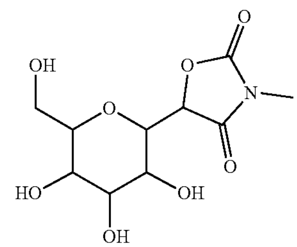 [SMILES: CN1C(=O)OC(C2OC(CO)C(O)C(O)C2O)C1=O] |
| 4a | 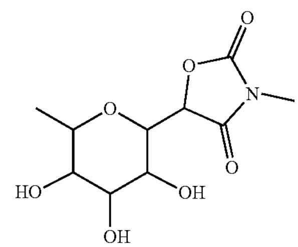 [SMILES: CC1OC(C2OC(=O)N(C)C2=O)C(O)C(O)C1O] |

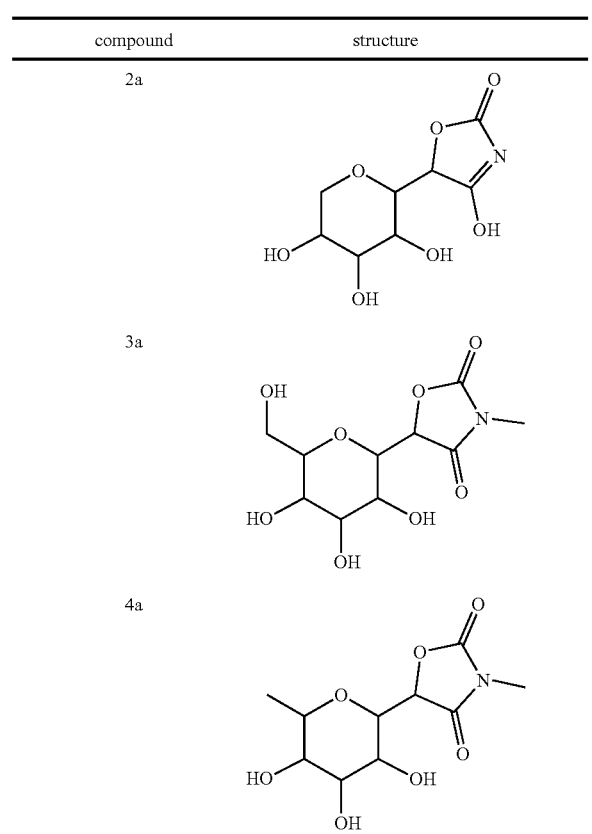

| compound | sugar | structure |
|---|---|---|
| 1 | D-glucose | 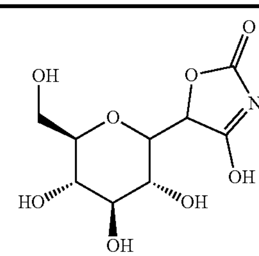 |
| 2 | D-xylose | 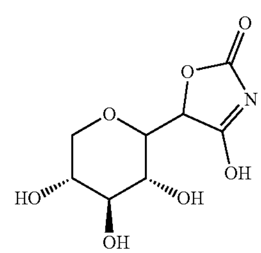 [SMILES: O=C1N=C(O)C(C2OC[C@@H](O)[C@H](O)[C@H]2O)O1] |
| 3 | D-glucose | 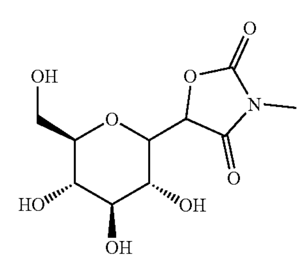 [SMILES: CN1C(=O)OC(C2O[C@H](CO)[C@@H](O)[C@H](O)[C@H]2O)C1=O] |

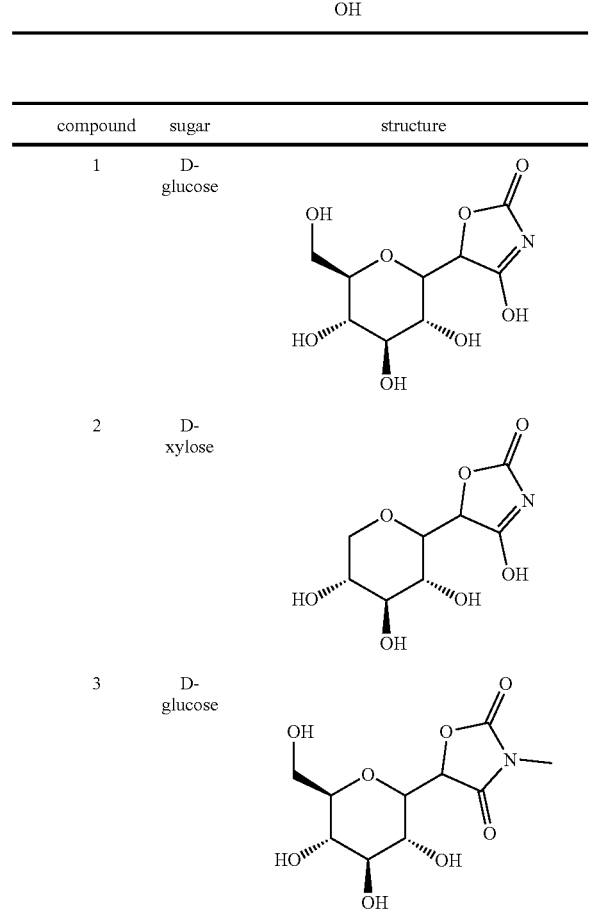

| compound | sugar | structure |
|---|---|---|
| 4 | L-rhamnose | 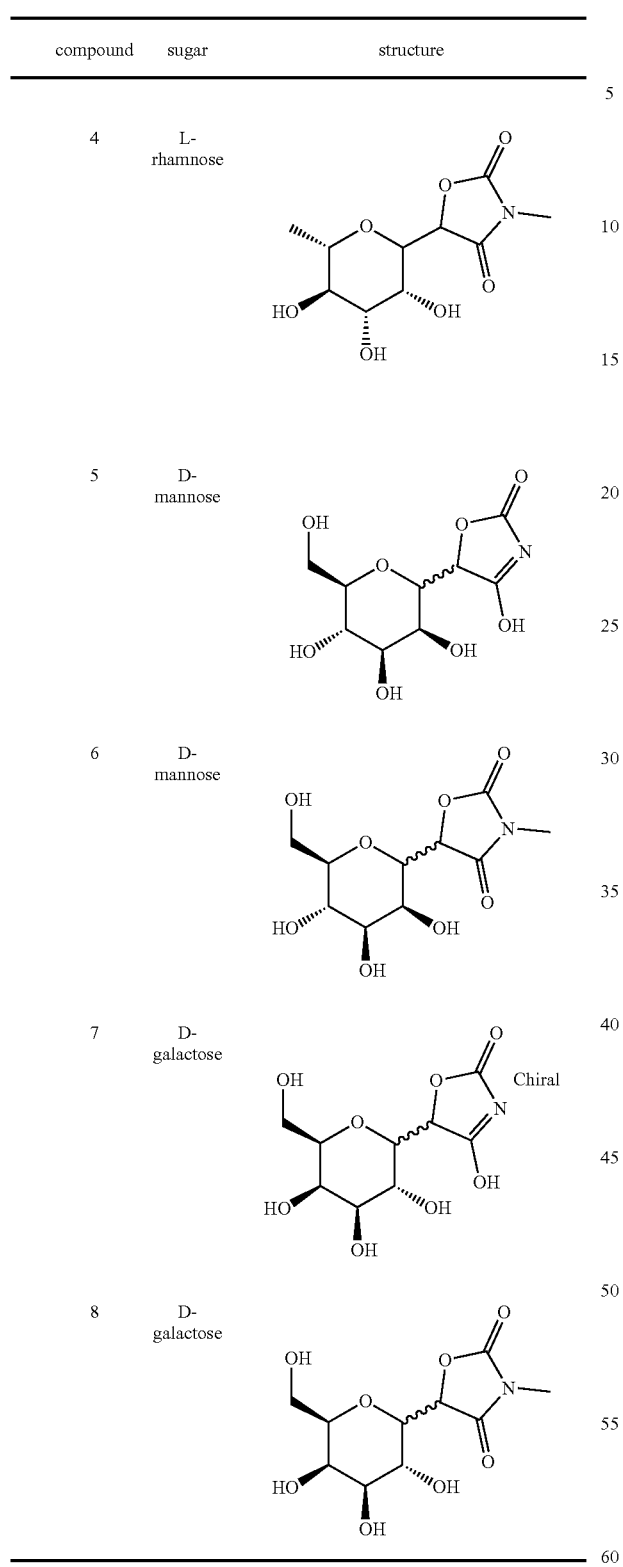 |
| 5 | D-mannose | 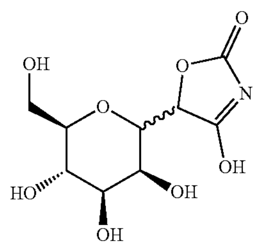 [SMILES: O=C1N=C(O)C(C2O[C@H](CO)[C@@H](O)[C@H](O)[C@@H]2O)O1] |
| 6 | D-mannose | 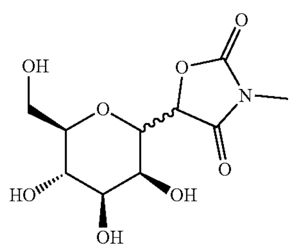 [SMILES: CN1C(=O)OC(C2O[C@H](CO)[C@@H](O)[C@H](O)[C@@H]2O)C1=O] |
| 7 | D-galactose | 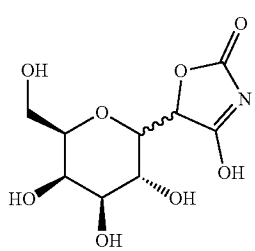 |
| 8 | D-galactose | 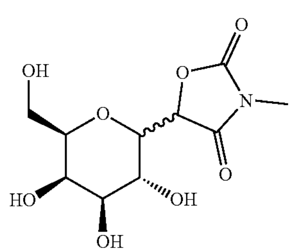 [SMILES: CN1C(=O)OC(C2O[C@H](CO)[C@H](O)[C@H](O)[C@H]2O)C1=O] |
and also the solvates thereof, and the organic or mineral base or acid salts thereof.
10. A composition comprising one or more compounds chosen from the compounds of formulae (I'), (I''), (I''''), (I'a), (I''a) and (I''''a) below:
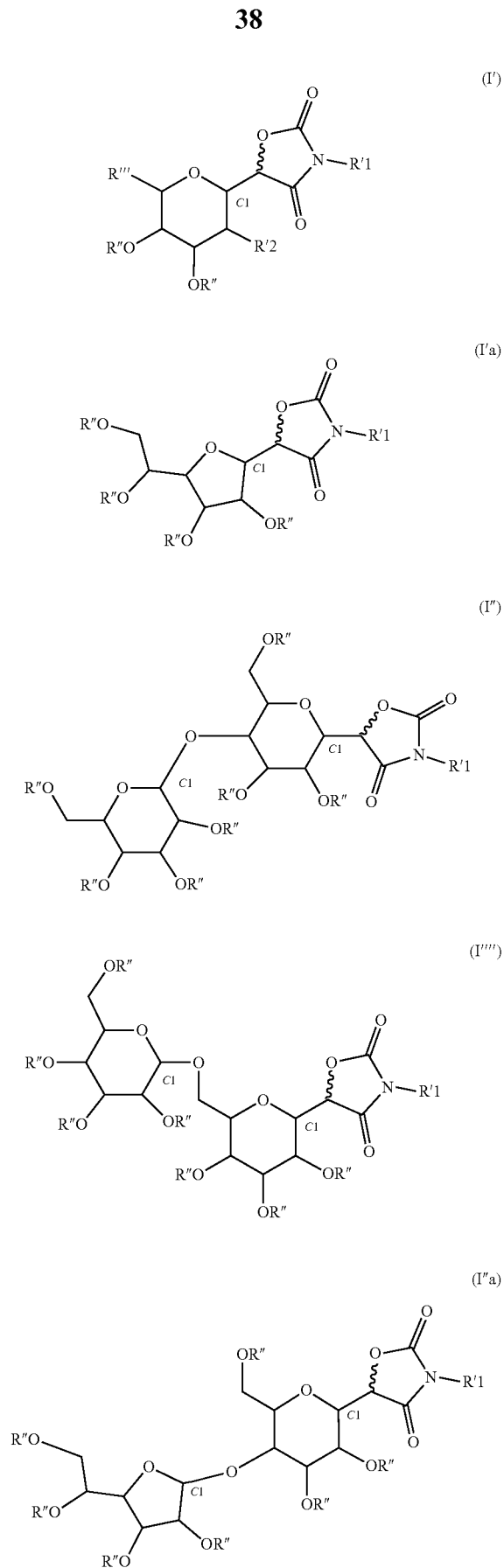

-continued

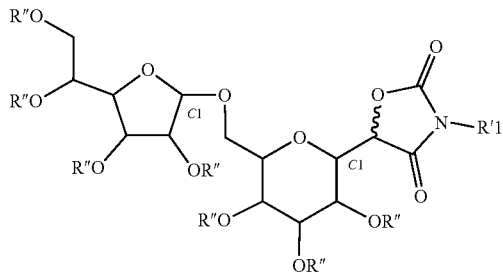

(I''''a)

and also the solvates thereof, the optical and geometric isomers and tautomers thereof and the salts thereof,
in which formulae (I'), (I''), (I'''), (I'a), (I''a) and (I''''a):
$R'_1$ represents
i) a hydrogen atom;
ii) a $(C_1-C_{18})$alkyl group;
iii) an aryl$(C_1-C_4)$alkyl group optionally substituted with at least one hydroxyl and/or $(C_1-C_4)$alkoxy group; or
iv) a cycloalkyl group);
$R'_2$ represents a hydrogen atom or the group —OR" with R" as defined below;
R" represents
i) $(C_1-C_6)$alkyl; or
ii) an acetyl radical; or
iii) a protective group (PG) for hydroxyl function(s); or
iv) a hydrogen atom;
R''' represents a hydrogen atom, or a $(C_1-C_4)$alkyl group, or a —CH$_2$—OR" group with R".

11. The composition according to claim 10, in which the one or more compound(s) are present in amounts ranging from 0.01% to 10% by weight relative to the total weight of the composition.

12. A composition comprising one or more 5-oxazolidine-2,4-dione C-glycoside derivatives corresponding to formula (I) below, and also the solvates thereof, the optical and geometric isomers and tautomers thereof and the organic or mineral base or acid salts thereof,

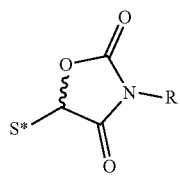

(I)

in which formula (I):
S* denotes a monosaccharide sugar radical or denotes a polysaccharide sugar radical comprising from 2 to 5 saccharide units, each saccharide unit (the saccharide unit in the case of a monosaccharide or each saccharide unit in the case of polysaccharides) comprising one or more hydroxyl groups optionally substituted with a radical R' chosen from:
i) $(C_1-C_6)$alkyl or $(C_2-C_6)$alkenyl; or
ii) an acetyl radical; or
iii) a protective group (PG) for hydroxyl function(s);
said monosaccharide radical possibly also being deoxygenated in position 2 (on its $C_2$ carbon atom);
said monosaccharide or polysaccharide radical possibly also comprising one or more amino groups $NR_bR_c$ with $R_b$ and $R_c$, which may be identical or different, representing a hydrogen atom, or an acetyl group, or a protective group for the amino function;
said monosaccharide or polysaccharide radical being connected to the rest of the molecule by a bond between the $C_1$ carbon atom of one of the sugars of said monosaccharide or polysaccharide radical, this bond possibly being α or β anomeric;
R represents
i) a hydrogen atom;
ii) a $(C_1-C_{18})$alkyl group;
iii) an aryl$(C_1-C_4)$alkyl group optionally substituted with at least one hydroxyl and/or $(C_1-C_4)$alkoxy group;
iv) a cycloalkyl group and one or more additional moisturizing active agents other than the compounds of formula (I).

13. A compound of formula (I) and also the solvates thereof, the optical and geometric isomers and tautomers thereof and the organic or mineral base or acid salts thereof,

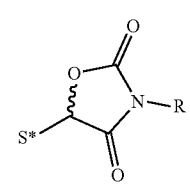

(I)

in which formula (I):
S* denotes a monosaccharide sugar radical or denotes a polysaccharide sugar radical comprising from 2 to 5 saccharide units, each saccharide unit (the saccharide unit in the case of a monosaccharide or each saccharide unit in the case of polysaccharides) comprising one or more hydroxyl groups optionally substituted with a radical R' chosen from:
i) $(C_1-C_6)$alkyl or $(C_2-C_6)$alkenyl; or
ii) an acetyl radical; or
iii) a protective group (PG) for hydroxyl function(s);
said monosaccharide radical possibly also being deoxygenated in position 2 (on its $C_2$ carbon atom);
said monosaccharide or polysaccharide radical possibly also comprising one or more amino groups $NR_bR_c$ with $R_b$ and $R_c$, which may be identical or different, representing a hydrogen atom, or an acetyl group, or a protective group for the amino function;
said monosaccharide or polysaccharide radical being connected to the rest of the molecule by a bond between the $C_1$ carbon atom of one of the sugars of said monosaccharide or polysaccharide radical, this bond possibly being α or β anomeric;
R represents
i) a hydrogen atom;
ii) a $(C_1-C_{18})$alkyl group;
iii) an aryl$(C_1-C_4)$alkyl group optionally substituted with at least one hydroxyl and/or $(C_1-C_4)$alkoxy group;
iv) a cycloalkyl group.

14. The compound of formula (I) according to claim 13, comprising a radical R chosen from:
i) a hydrogen atom;
ii) a $(C_1-C_{18})$alkyl group.

15. A cosmetic process for moisturizing keratin materials which comprises applying to said keratin materials a composition as defined in claim 10.

16. The cosmetic process according to claim 15, wherein said composition is applied to dry skin and/or to a cutaneous region chosen from:
the hands,
the face,
the neck,
the feet,
the legs,
the arms and forearms.

17. A process for the synthesis of compounds of formula (I),

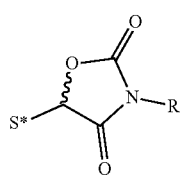
(I)

in which formula (I):
S* denotes a monosaccharide sugar radical or denotes a polysaccharide sugar radical comprising from 2 to 5 saccharide units, each saccharide unit (the saccharide unit in the case of a monosaccharide or each saccharide unit in the case of polysaccharides) comprising one or more hydroxyl groups optionally substituted with a radical R' chosen from:
i) $(C_1-C_6)$alkyl or $(C_2-C_6)$alkenyl; or
ii) an acetyl radical; or
iii) a protective group (PG) for hydroxyl function(s);
said monosaccharide radical possibly also being deoxygenated in position 2 (on its $C_2$ carbon atom);
said monosaccharide or polysaccharide radical possibly also comprising one or more amino groups $NR_bR_c$ with $R_b$ and $R_c$, which may be identical or different, representing a hydrogen atom, or an acetyl group, or a protective group for the amino function;
said monosaccharide or polysaccharide radical being connected to the rest of the molecule by a bond between the $C_1$ carbon atom of one of the sugars of said monosaccharide or polysaccharide radical, this bond possibly being α or β anomeric;
R represents
i) a hydrogen atom;
ii) a $(C_1-C_{18})$alkyl group;
iii) an aryl$(C_1-C_4)$alkyl group optionally substituted with at least one hydroxyl and/or $(C_1-C_4)$alkoxy group;
iv) a cycloalkyl group,
according to scheme (1) below:

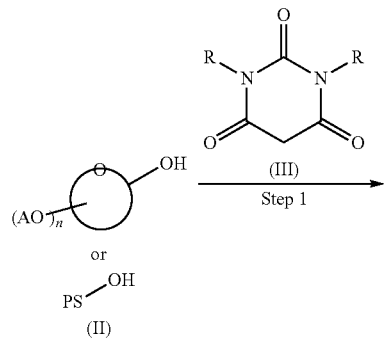

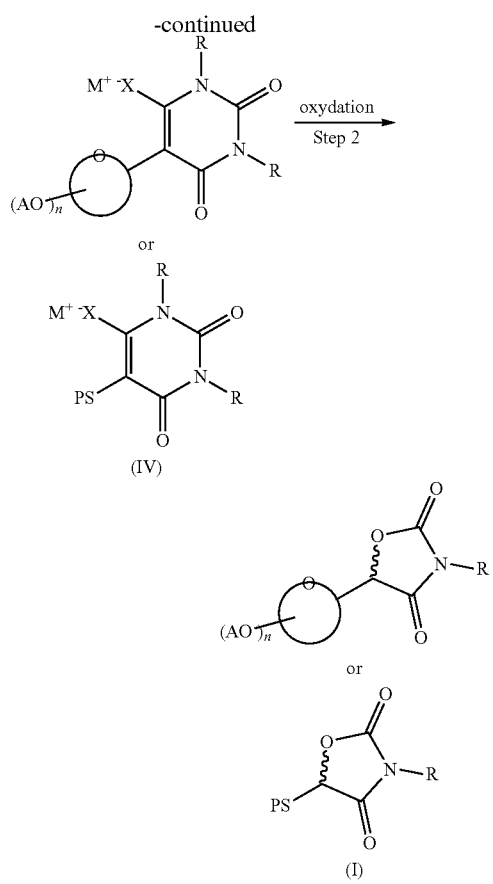

in which (II) denotes a monosaccharide represented by:

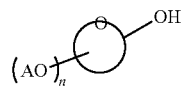

or a polysaccharide PS—OH, in which Ra represents a hydrogen atom, a (C1-C4)alkyl group or a (poly)hydroxy(C1-C4)alkyl group or the hydroxyl function(s) of the (poly)hydroxy(C1-C4)alkyl group being substituted with A;
it being understood that the $R_a$ radical is in the $C_5$ position if the sugar unit is in pyranose form or in the $C_4$ position if it is in furanose form;
$R_b$ representing a hydrogen atom or a $(C_1-C_4)$alkyl group;
$R_c$ representing a hydrogen atom, or a protective group for the amine function-;
$R_e$ represents a hydrogen atom or a —$CH_2$—O—A group;
A representing a hydrogen atom, a $(C_1-C_6)$alkyl group or a hydroxyl-function-protective group, or else, when n is greater than or equal to 2 and two groups A-O are contiguous, then two A groups can together form a linear or branched $(C_1-C_6)$alkylene chain;
n is equal to 1, 2 or 3 and m is equal to 0 or 1, p' and q' representing an integer inclusively between 0 and 4, with p'+q' inclusively between 0 and 4 it being understood that the two units between square brackets can be reversed; PS—OH denoting a polysaccharide having the structure (gg) below:

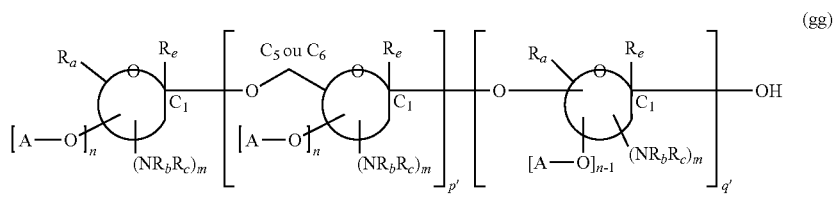

step 1 comprising reacting a monosaccharide or a polysaccharide PS—OH of formula (II) with a barbituric acid derivative (III) by heating optionally at a temperature of between 30° C. and 100° C., so as to give the compound comprising a sugar unit (IV);

step 2 comprising reacting the compound (IV) with a chemical oxidizing agent or else a biological agent, it being understood that, if A represents a hydrogen atom and it is desired to have a protective group PG, then a protection step is added, that, if $R_b$ and $R_c$ of $NR_bR_c$ optionally present on the monosaccharide or the polysaccharide (II) represent hydrogen atoms and it is desired to protect the amino group(s), a protection step is carried out, that, if the group R comprises a function sensitive to these synthesis steps, a protection/deprotection sequence is added, wherein, under certain reaction temperature and time conditions during step 2, optionally the intermediate (V) according to step 2a is isolated:

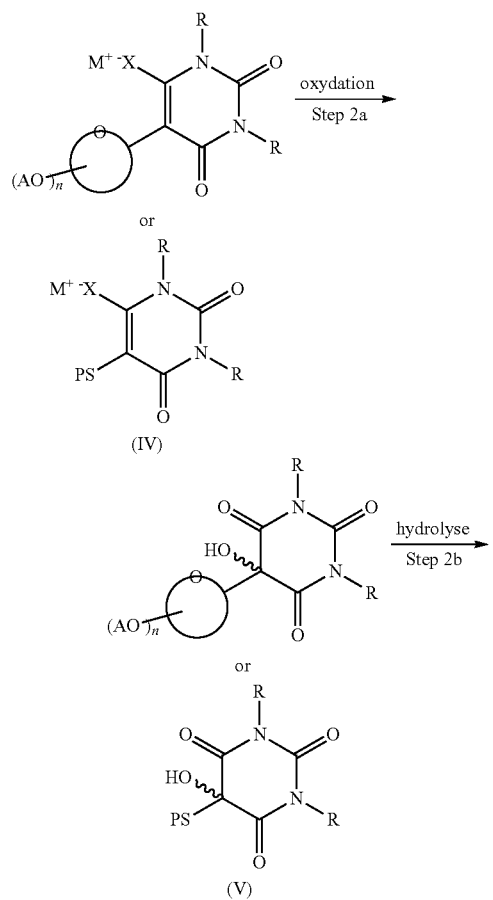

-continued

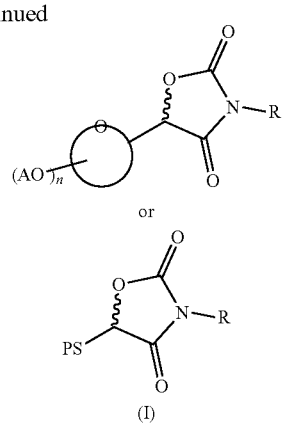

wherein step 2b comprises treating the compound (V) in a polar solvent or solvent mixture) with a boiling point of between 40° C. and 100° C. at atmospheric pressure to give a C-glycoside compound of formula (I).

18. A compound of formula (V), and also the solvates and/or isomers and/or salts thereof, having the general formula below

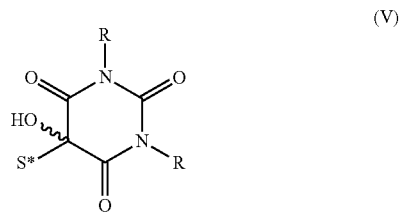

wherein—S* denotes a monosaccharide sugar radical or denotes a polysaccharide sugar radical comprising from 2 to 5 saccharide units, each saccharide unit (the saccharide unit in the case of a monosaccharide or each saccharide unit in the case of polysaccharides) comprising one or more hydroxyl groups optionally substituted with a radical R' chosen from:

i) $(C_1-C_6)$alkyl or $(C_2-C_6)$alkenyl; or
ii) an acetyl radical; or
iii) a protective group (PG) for hydroxyl function(s);

said monosaccharide radical possibly also being deoxygenated in position 2 (on its $C_2$ carbon atom);

said monosaccharide or polysaccharide radical possibly also comprising one or more amino groups $NR_bR_c$ with $R_b$ and $R_c$, which may be identical or different, representing a hydrogen atom, or an acetyl group, or a protective group for the amino function;

said monosaccharide or polysaccharide radical being connected to the rest of the molecule by a bond between the $C_1$ carbon atom of one of the sugars of said monosaccharide or polysaccharide radical, this bond possibly being α or β anomeric; and R represents i) a hydrogen atom;
ii) a $(C_1$-$C_{18})$alkyl group;
iii) an aryl$(C_1$-$C_4)$alkyl group optionally substituted with at least one hydroxyl and/or $(C_1$-$C_4)$alkoxy group;
iv) a cycloalkyl group.

19. The compound according to claim 18, which is

| compound | sugar | structure |
|---|---|---|
| 9 | D-glucose | 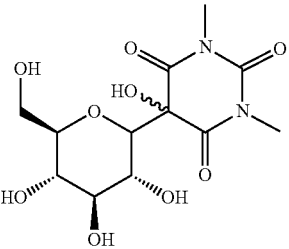 [SMILES: CN1C(=O)N(C)C(=O)C(O)(C2O[C@H](CO)[C@@H](O)[C@H](O)[C@H]2O)C1=O] |

20. The process according to claim 1 wherein the keratin material is skin.

* * * * *